United States Patent
Coleman et al.

(10) Patent No.: US 9,855,048 B2
(45) Date of Patent: Jan. 2, 2018

(54) CONTROLLING A SIZE OF A PYLORUS

(71) Applicants: James E. Coleman, Dublin (IE);
Christy Cummins, Johnstown Naas (IE)

(72) Inventors: James E. Coleman, Dublin (IE);
Christy Cummins, Johnstown Naas (IE)

(*) Notice: Subject to any disclaimer, the term of this patent is extended or adjusted under 35 U.S.C. 154(b) by 215 days.

(21) Appl. No.: 14/547,557

(22) Filed: Nov. 19, 2014

(65) Prior Publication Data
US 2015/0142111 A1 May 21, 2015

Related U.S. Application Data

(60) Provisional application No. 61/906,727, filed on Nov. 20, 2013.

(51) Int. Cl.
*A61F 5/00* (2006.01)
*A61B 17/12* (2006.01)
(Continued)

(52) U.S. Cl.
CPC .... *A61B 17/12031* (2013.01); *A61B 17/0057* (2013.01); *A61B 17/12109* (2013.01);
(Continued)

(58) Field of Classification Search
CPC .............. A61F 2250/001; A61F 2/2436; A61F 2220/0008; A61F 2220/0075;
(Continued)

(56) References Cited

U.S. PATENT DOCUMENTS

2002/0055757 A1* 5/2002 Torre ............... A61B 17/12099
606/192
2003/0078604 A1* 4/2003 Walshe .............. A61B 17/0401
606/151
(Continued)

FOREIGN PATENT DOCUMENTS

CN 102470038 A 5/2012
CN 102647957 A 8/2012
(Continued)

OTHER PUBLICATIONS

Invitation to Pay Additional Fees for Application No. PCT/EP2014/075203, 5 pages, dated Feb. 12, 2015.

*Primary Examiner* — Navin Natnithithadha
*Assistant Examiner* — Sunita Reddy
(74) *Attorney, Agent, or Firm* — Mintz Levin Cohn Ferris Glovsky and Popeo, P.C.

(57) ABSTRACT

Systems and methods are provided for reversibly controlling a size and/or restricting the movement of a body orifice, such as a pyloric opening, using an implantable device configured to allow a distance between opposed ends thereof to be adjusted. A device is provided having attachment members and a connector portion extending therebetween and configured such that a size of the pyloric opening is decreased upon the implantation of the device. The connector can be adjustable to allow a size of the pyloric opening to be adjusted after it has been restricted. The connector can include two or more bridge portions having different lengths such that cutting a first bridge portion can increase the distance between the attachment members so as to increase the size of the pyloric opening. To revert to a natural size of the body orifice, the entire connector can be cut or otherwise broken and/or removed.

16 Claims, 11 Drawing Sheets

(51) Int. Cl.
*A61B 17/00* (2006.01)
*A61F 2/24* (2006.01)
*A61B 17/42* (2006.01)

(52) U.S. Cl.
CPC .......... *A61F 2/2418* (2013.01); *A61F 2/2436* (2013.01); *A61F 5/0079* (2013.01); *A61B 2017/00389* (2013.01); *A61B 2017/00606* (2013.01); *A61B 2017/00623* (2013.01); *A61B 2017/00778* (2013.01); *A61B 2017/00986* (2013.01); *A61B 2017/12004* (2013.01); *A61B 2017/12054* (2013.01); *A61B 2017/4233* (2013.01); *A61F 2220/0008* (2013.01); *A61F 2220/0075* (2013.01); *A61F 2250/001* (2013.01); *A61F 2250/0008* (2013.01); *A61F 2250/0098* (2013.01)

(58) Field of Classification Search
CPC ............ A61F 2250/0008; A61F 5/0079; A61F 2250/0098; A61F 2/2418; A61B 2017/00389; A61B 2017/12054; A61B 2017/4233; A61B 17/12109; A61B 17/12031; A61B 2017/00778; A61B 2017/00606; A61B 2017/12004; A61B 2017/00623; A61B 2017/00986; A61B 17/0057

USPC .......................................... 623/14.13; 600/37
See application file for complete search history.

(56) References Cited

U.S. PATENT DOCUMENTS

| 2005/0192615 | A1* | 9/2005 | Torre ............... A61B 17/12099 606/192 |
| 2007/0185529 | A1* | 8/2007 | Coleman ............ A61B 17/0057 606/213 |
| 2007/0270943 | A1 | 11/2007 | Solem et al. |
| 2009/0312597 | A1* | 12/2009 | Bar .................. A61B 17/00234 600/37 |
| 2010/0114128 | A1* | 5/2010 | Coleman ................ A61B 17/11 606/153 |
| 2011/0040232 | A1* | 2/2011 | Magal ..................... A61F 5/003 604/8 |
| 2011/0276091 | A1 | 11/2011 | Melanson et al. |

FOREIGN PATENT DOCUMENTS

| WO | WO-2002035980 A2 | 5/2002 |
| WO | WO-2006111961 A2 | 10/2006 |
| WO | WO-2009130619 A1 | 10/2009 |
| WO | 2013112450 A1 | 8/2013 |

* cited by examiner

CONTROLLING A SIZE OF A PYLORUS

CROSS REFERENCE

The present application claims priority to U.S. Provisional Application No. 61/906,727 entitled "Surgical Implant Devices, Systems, and Methods," filed on Nov. 20, 2013, which is hereby incorporated herein by reference in its entirety.

FIELD

Systems and methods are provided for controlling a size of a body orifice, such as a pyloric orifice.

BACKGROUND

Rates of obesity are steadily increasing in the United States and other countries. Obesity has been linked to many serious conditions such as heart disease, diabetes, joint disorders, increased cancer rates, and even death.

Obesity can be treated using a variety of approaches that lead to weight reduction. Bariatric surgery and other similar approaches have been used to help patients lose weight. However, such surgeries are generally invasive and can be associated with multiple complications and risks. Also, patients can develop gallstones and nutritional deficiencies. Furthermore, some common bariatric surgeries, such as a gastric bypass procedure, are irreversible. Moreover, the success of the surgeries depends on the patient making dramatic lifelong changes, such as consumption of special foods and intake of vitamins and certain medications. If a patient does not comply with the required lifestyle adjustments, results of the surgery can be compromised and health complications can arise.

Accordingly, there remains a need for more efficient and less invasive approaches for facilitating weight loss.

SUMMARY

Various methods and devices for controlling a size of an orifice are provided. In one embodiment, a device is provided having a first attachment member configured to mate to a first deployable implant, a second attachment member configured to mate to a second deployable implant, and a connector coupled between the first and second attachment members. The connector can include a first portion having a first length such that the first and second attachment members are held at a first distance apart, and a second portion having a second length that is greater than the first length. The first portion can be configured to be cut such that the first and second attachment members can be held at a second distance apart that is greater than the first distance.

While the device can have a variety of configurations, in one embodiment at least one of the first and second attachment members can be a loop. For example, the first attachment member can be in the form of a first loop formed at a first terminal end of the connector, and the second attachment member can be in the form of a second loop formed at a second terminal end of the connector. The connector can also vary, and in one embodiment the connector can include an elongate spine having the first and second attachment members coupled thereto. The first portion can be formed from a portion of the elongate spine, and the second portion can include opposed ends coupled to the elongate spine at opposed ends of the first portion. In other aspects, the first portion can be positioned between opposed ends of the second portion of the connector. The connector can also include a third portion having a third length that is greater than the second length. The second portion can be configured to be cut such that the first and second attachment members can be held at a third distance apart that is greater than the second distance.

In another embodiment, a system for controlling a size of an orifice is provided and includes a first implant configured to be implanted within tissue, a second implant configured to be implanted within tissue, and a connector having a first end coupled to the first implant and a second end coupled to the second implant. The connector can include a first bridge portion extending between the first and second ends and having a first length. The first bridge portion can be configured to maintain the first and second implants at a first distance apart. The connector can also include a second bridge portion extending between the first and second ends and having a second length that is greater than the first length. The second bridge portion can be configured to maintain the first and second implants at a second distance apart. The first bridge portion can be configured to be cut to allow the first and second implants to move from the first distance apart to the second distance apart.

In certain aspects, the connector can include at least one loop formed thereon for slidably receiving one of the first and second implants. For example, the connector can include a first loop formed on the first end thereof for slidably receiving the first implant, and a second loop formed on the second end thereof for slidably receiving the second implant.

In other embodiments, the device can include a third bridge portion extending between the first and second ends and having a third length that is greater than the second length. The third bridge portion can be configured to maintain the first and second implants at a third distance apart. With the first bridge portion cut, the second bridge portion can be configured to be cut to allow the first and second implants to move from the second distance apart to the third distance apart. In other aspects, the first bridge portion can be positioned between opposed ends of the second bridge portion.

In another embodiment, a method of controlling a size of a body orifice is provided and can include implanting a first deployable implant into tissue at a first location on a first side of an orifice, implanting a second deployable implant into tissue at a second location on a second side of the orifice such that a first bridge portion of a connector extending between the first implant and the second implant maintains the first and second locations at a first distance apart, and cutting the first bridge portion such that a second bridge portion of the connector maintains the first and second locations at a second distance apart that is greater than the first distance. The method can also include, after cutting the first bridge portion, cutting the second bridge portion such that a third bridge portion of the connector maintains the first and second locations at a third distance apart that is greater than the second distance. The method can further include, after cutting the second bridge portion, cutting the third bridge portion such that the implant does not maintain a distance between the first and second locations of the orifice.

In other aspects, implanting the first implant can include deploying proximal and distal deployable wings of the first implant to engage tissue therebetween, and implanting the second implant comprises deploying proximal and distal deployable wings of the second implant to engage tissue therebetween. In other embodiments, the first connector can be mated to the first and second implants via respective first and second attachment members. The method can also include, prior to implanting, delivering the first deployable implant to the body orifice with the connector coupled to the first deployable implant and mounted on a delivery shaft coupled to the first deployable implant. The method can further include implanting a third deployable implant into tissue at a third location on the orifice such that a first bridge portion of a second connector extending between the second implant and the third implant maintains a third distance between the second and third locations.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1A:
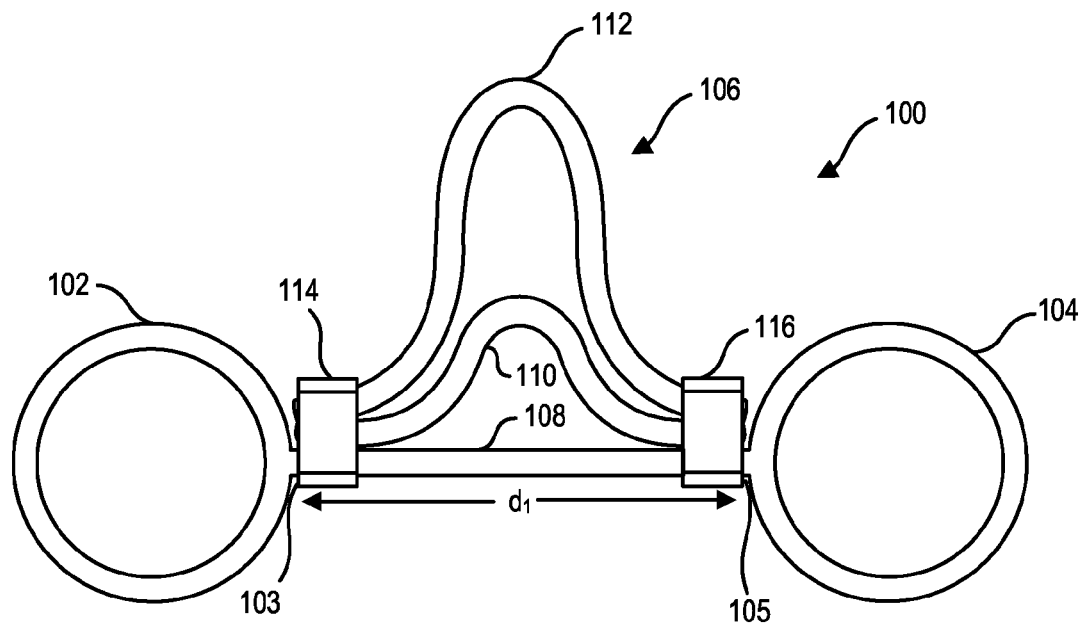
FIG. 1A is a perspective view of one embodiment of a device having a connector in its initial configuration to maintain a first distance between attachment members.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. Further, the features illustrated or described in connection with one exemplary embodiment may be combined with the features of other embodiments. Such modifications and variations are intended to be included within the scope of the present invention.

Methods and devices are provided for treating obesity and other associated conditions, such as, for example, type 2 diabetes mellitus, in a non-invasive and safe manner. In particular, the described techniques utilize devices for controlling a size of an opening of a pylorus. The pylorus is a sphincter that sits between the stomach and a first section of the small intestine, the duodenum. The pylorus has two parts, the pyloric antrum that opens to the body of the stomach, and the pyloric canal opening to the duodenum. The pyloric canal ends at the pyloric orifice, or opening, that marks the junction between the stomach and the duodenum. The pylorus lets food pass from the stomach to the duodenum and controls gastric emptying that results from contractile activity of the stomach and pylorus.

A gastric pyloric restriction involves narrowing of a pylorus and can increase a time period during which food remains in the stomach, leading to a delay in gastric emptying. This can induce or increase the feeling of satiation in a patient such that the patient may be less inclined to consume excessive amounts of food. Such a decrease in food intake and calorie consumption can ultimately contribute to weight loss and facilitate obesity treatment.

The methods and devices disclosed herein can be used to control a size of a pyloric opening, i.e., a size of an open area of the pylorus that allows food to pass therethrough from a stomach to a small intestine. The device can be applied to narrow and, if desired, to subsequently widen the pyloric opening. In addition, the methods and devices described herein can be used to reduce peristaltic motion in the area of the pyloric opening to slow the transfer of food through the opening. The procedure using the described device is simple, less invasive than existing approaches, efficient, and can be entirely reversible. Thus, if no restriction on the size of the pyloric opening is needed, the device can be manipulated such that the pyloric opening is restored to its natural size and becomes fully open. A person having ordinary skill in the art will appreciate that while methods and devices are described herein for narrowing the pylorus, the devices and methods can be used to adjust a size of any orifice.

In general, the device can include a connector portion coupled between attachment members. The attachment members can be configured to mate to respective deployable implants that can be affixed into tissue. In this way, the device can be delivered to an implantation site at a pyloric opening or other body orifice and can be held at that site by the implants once they are deployed. The device can be positioned at the opening such that the connector portion spans the opening and is thereby used to control the size of the opening. In addition to adjusting the size of the opening, the device can slow down or prevent peristalsis from occurring thereby slowing the transfer of food through the pyloric opening. The connector portion can be adjusted in length to adjust a size of the opening.

Figure 1B:
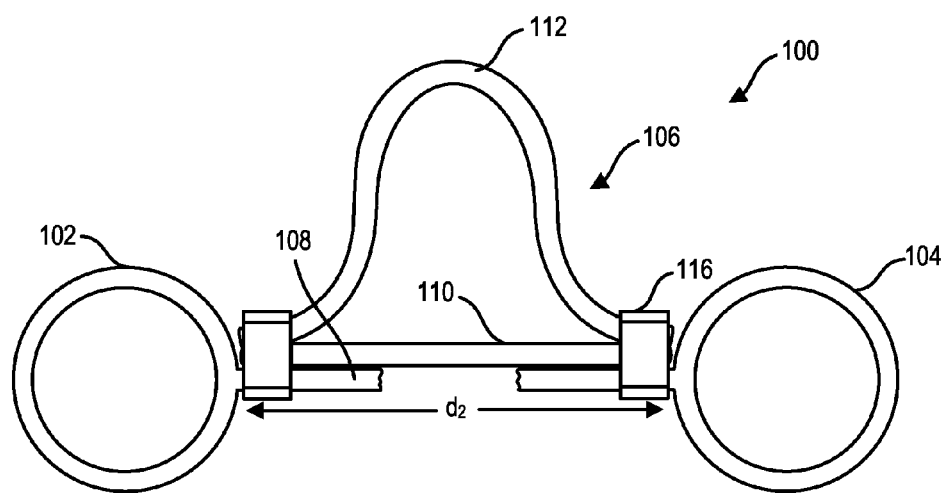
FIG. 1B is another perspective view of the device of FIG. 1A having the connector in a second configuration to maintain a second distance between the attachment members.
Figure 1C:
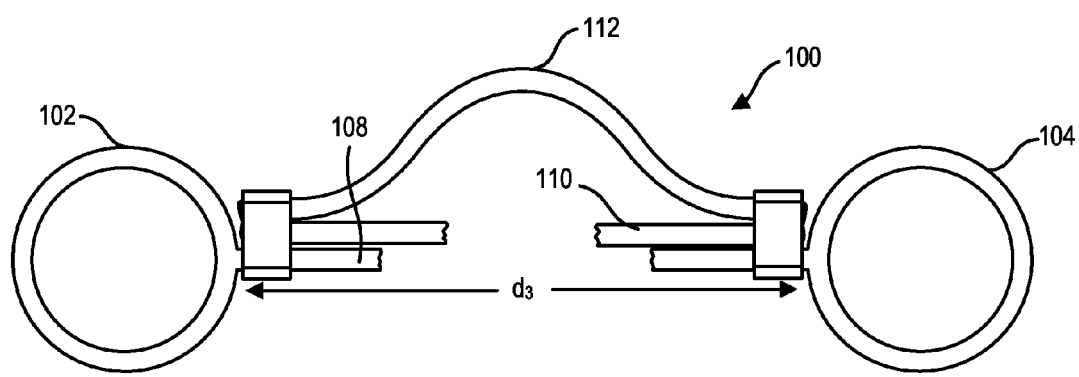
FIG. 1C is another perspective view of the device of FIG. 1A having the connector in a third configuration to maintain a third distance between the attachment members.

FIGS. 1A-1C illustrate one embodiment of a device 100 for controlling a size of a body orifice, such as a pyloric orifice, or opening. The illustrated device 100 includes a first attachment member 102, a second attachment member 104, and a bridge or connector 106 coupled between the between the first and second attachment members 102, 104 at first and second ends 103, 105 of the connector 106.

As shown in FIG. 1A, the first attachment member 102 is disposed at the first end 103 of the connector 106, and the second attachment member 104 is disposed at the second end 105 of the connector 106. The first attachment member 102 can be configured to mate to a first deployable implant, and the second attachment member 104 can be configured to mate to a second deployable implant. In this embodiment, the first and second attachment members 102, 104 are shown as rings or loops that can removably and slidably receive a respective deployable implant. The loops can be formed from various materials and can have varying degrees of flexibility/rigidity and/or elasticity. In an exemplary embodiment, the loops are flexible and optionally elastic for ease of mating to implants of varying sizes. It should be appreciated that the attachment members can have any other configuration that allows them to receive a respective deployable implant such that the implant can be delivered to, and maintained at, a surgical site while being engaged with the attachment member.

The connector 106 can also have various configurations. In the illustrated embodiment, the connector 106 has multiple elongate bridge portions extending between the attachment members 102, 104 and having different lengths. For example, as shown in FIG. 1A, the connector 106 includes a first portion 108 having a first length, a second portion 110 having a second length, and a third portion 112 having a third length. In this embodiment, the first portion 108 is the shortest, the second portion 110 is longer than the first portion 108, and the third portion 112 is the longest among the portions 108, 110, 112. As shown in FIGS. 1A-1C, the first portion 108 can be fixedly attached to the first and second attachment members 102, 104. In some embodiments, the first portion 108 can be integrally formed with the attachment members 102, 104. However, the first portion 108 can be attached to the attachment members 102, 104 in any suitable manner. The second and third portions 110, 112 can be coupled to the first portion 108 via clamping elements 114, 116 positioned at the first and second ends 103, 105 of the connector 106. In the embodiment illustrated in FIGS. 1A-1C, the second and third portions 110, 112 are coupled to the first portion 108 while not being directly coupled to the attachment members 102, 104. However, it should be appreciated that, in other embodiments, the second and third portions 110, 112 can additionally or alternatively be directly coupled to the attachment members 102, 104.

In some embodiments, one or more of the first, second, and third portions 108, 110, 112 can be formed from a single elongate component (e.g., a suture, cord, wire, or any other component). Furthermore, the lengths of one or more of the portions 108, 110, 112 can be adjustable to accommodate for different patient's anatomical characteristics, such as a natural size of the orifice to be controlled, a desirable decrease of the size, and other factors. Thus, prior to delivering the device 100 into a subject, a surgeon or other medical professional can manipulate the connector 106 such that the first, second, and third portions 108, 110, and 112 have desirable lengths. For example, the clamping elements 114, 116 can be configured to be loosened to allow the lengths of one or more of the portions 108, 110, and 112 to be adjusted and then to be tightened prior to deployment of the device 100. However, in some embodiments, the device 100 can be manufactured in a ready-to-deploy configuration such that no further adjustments to any dimension of the device may be required prior to insertion of the device into a body.

The connector 106 can be configured to function as a bridge that holds the attachment members 102, 104 at a certain distance apart. In some embodiments, to adjust the distance between the attachment members 102, 104, the bridge portions 108, 110, 112 of the connector 106 can be cut, broken, or otherwise altered. It should be appreciated that the connector 106 of the device 100 is shown herein to include the three bridge portions 108, 110, 112 by way of example only, as the connector 106 can have any suitable number of bridge portions (e.g., two, four, five, etc.), having any suitable configurations and lengths, as embodiments are not limited in this respect. The first, second, and third portions 108, 110, 112 can have different lengths. By way of a non-limiting example, each portion can have a length in the range of from about 1 mm to about 10 mm.

In some embodiments, a length of a longest portion of the connector 106 can be less than a natural diameter of the pyloric opening or other opening intended to be controlled using the device 100, such that the opening can be restricted. The lengths of the portions 108, 110, 112 can be selected so that the connector 106 can maintain a pylorus in a partially closed state, which allows solid food of a certain size to pass into the small intestine while delaying solid food of a larger size in the stomach. In this way, a rate of gastric emptying can be controlled in different ways, for example, depending on desired weight loss goals, patient's characteristics, and any other factors.

In some embodiments, two or more portions of the connector 106 can have the same lengths. Furthermore, it should be appreciated that specific shapes of the first, second, and third portions 108, 110, 112 in FIGS. 1A-1C are shown by way of example, and the portions 108, 110, 112 can have any suitable sizes and configurations.

The first, second, and third portions 108, 110, 112 of the connector 106 can be formed from the same or different material that is used to form the attachment members 102, 104. In some embodiments, the bridge portions 108, 110, 112 of the connector 106 and/or other components of the device 100, such as the attachment members 102, 104, can be formed from a flexible, durable, and pliable material that can be cut using an appropriate surgical instrument while the device 100 is held at the orifice in the patient's body. While the material can be non-elastic, in other embodiments, the material can be elastic. For example, each connector portion can have differing degrees of elasticity to provide a desired length when tension is provided therein.

Additionally or alternatively to being able to be cut, one or more of the portions 108, 110, 112 can be made such that they can be broken, stretched or otherwise altered such that their integrity is destroyed or interrupted. The material can be configured to be cut or otherwise broken in an atraumatic manner such that when one or more of the portions 108, 110, 112 are cut, the thus formed free ends of the cut portion(s) do not cause trauma or any unreasonable inconvenience to the patient. The material can be, for example, a suture fabric, that can be formed from a polymer, natural fiber, any combination thereof, or any other suitable material such as a stainless steel, titanium, and/or a precious metal. In some embodiments, one or more of the portions 108, 110, 112 can be biodegradable. For example, one or more of the portions 108, 110, 112 can be selectively biodegradable such that they can disintegrate at different rates, which can be selected in any suitable manner, to thereby control a size of the body orifice.

In use, one or more of the portions 108, 110, 112 of the connector 106 can be configured to be cut or otherwise broken, or removed, to change the distance between the attachment members 102, 104. For example, in the configuration of the device 100 shown in FIG. 1A, when all three portions 108, 110, 112 are intact, the attachment members 102, 104 can be held at a first distance $d_1$ apart. The first distance can depend on the length of the first portion 108 which is the shortest portion of the connector 106. For example, the first distance can be equal or substantially equal to the first length of the first portion 108.

When the first portion 108 is cut, the attachment members 102, 104 can be held at a second distance $d_2$ apart that is greater than the first distance $d_1$, as shown in FIG. 1B. The second distance $d_2$ can be equal or substantially equal to the length of the portion 110 that is the second longest portion of the connector 106. In this way, the distance between the attachment members 102, 104 can be increased, as schematically shown in FIG. 1B. If it is desired to further increase the distance between the attachment members 102, 104, the portion 110 can be similarly cut or otherwise broken such that the distance between the attachment members 102, 104 becomes dependent on the length of the third portion 112, which is the longest portion of the connector 106. In particular, as shown in FIG. 1C, when both of the first and second portions 108, 110 are cut, the attachment members 102, 104 can be held at a third distance $d_3$ apart that can depend on the length of the third portion 112 which is now the only portion holding the attachment members 102, 104 together. If no restriction on the size of the body orifice is required, the third portion 112 can also be cut or broken such that the device 100 no longer imposes any restrictions to the size of the orifice. The method of using the device 100, for example, to narrow a pyloric opening, is described in more detail below.

Figure 2:
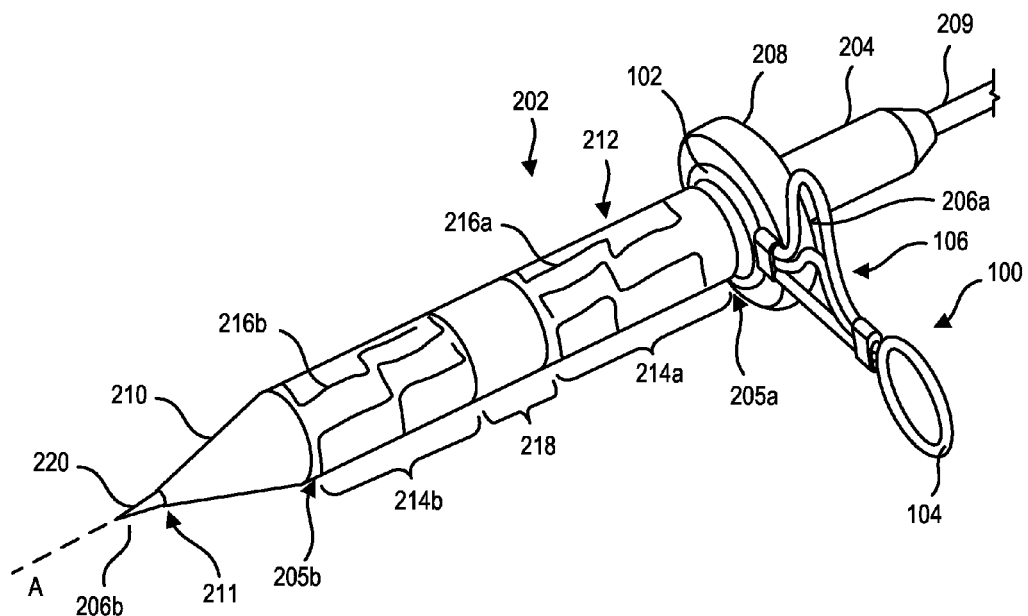
FIG. 2 is a perspective side view of the device of FIG. 1A having a first deployable implant attached thereto prior to deployment of the first implant.

The device 100 can be configured to mate with one or more deployable implants. FIG. 2 illustrates a first deployable implant 202 in an undeployed configuration for anchoring the device 100 at the body orifice to control a size thereof, in accordance with some embodiments. A person skilled in the art will appreciate that any anchor can be used to secure the device 100 to tissue. It should be appreciated that the implant 202 and any other implants that can be used in conjunction with the described techniques, as well as devices, systems and methods used to deliver and deploy the implants (e.g., an introducer used to deliver the implant(s) into a body), can include any components configured as described at least in U.S. Pat. No. 7,625,392 entitled "Wound closure devices and methods," issued Dec. 1, 2009, U.S. Pat. No. 8,197,498 entitled "Gastric bypass devices and procedures," issued Jun. 12, 2012, U.S. Patent Application Publication No. 2009/0105733, entitled "Anastomosis devices and methods," filed Oct. 22, 2007, and U.S. Patent Application Publication No. 2013/0165963, entitled "Devices and Methods for Occluding or Promoting Fluid Flow," filed Dec. 21, 2011, the contents of each of which are incorporated herein by reference in their entireties.

FIG. 2 shows the first deployable implant 202 having proximal and distal ends 206a, 206b, and being detachably coupled to a guide member 204 at the proximal end 206a. As used herein, "proximal" refers to an end or portion that is closer to a hand of an operator (e.g., surgeon) controlling operation of the described devices, such as the implant 202. "Distal" refers to an end or portion that is farther away from the operator and is nearer a surgical site. As shown in FIG. 2, the guide member 204 can be an elongate tube and can be part of a delivery assembly used to deliver the implant 202 to the implantation site. As further shown in FIG. 2, the implant 202 can include a collar 208 disposed at the proximal end 206a thereof. The implant 202 can be coupled (e.g., slidably) to the attachment member 102 at the proximal end 206a thereof. For example, prior to being delivered and affixed into tissue, the implant 202 can slide with its distal end 206b through the loop of the attachment member 102 such that the loop lies against the collar 208 to prevent further advancement of the implant 202 through the attachment member 102.

The implant 202 can have a generally elongate tubular body 212 having proximal and distal ends 205a, 205b. The implant 202 further includes proximal and distal portions 214a, 214b that are configured to expand to engage tissue therebetween. As illustrated in the undeployed implant 202 of FIG. 2, the proximal and distal portions 214a, 214b include a plurality of slits 216a, 216b, respectively, formed therein and configured to allow portions of the elongate tubular body 212 between the plurality of slits 216a, 216b to radially expand. A mid-portion 218 of the tubular body 212, located between the proximal and distal portions 214a, 214b, can be configured, when the implant 202 is deployed, to be positioned so as to span a wall of the tissue into which the implant 202 is affixed. The mid-portion 218 can have a fixed or adjustable length. For example, the length of the mid-portion 218 can be changed to correspond to a thickness of a tissue wall.

The slits 216a, 216b in the proximal and distal portions 214a, 214b can extend in any direction, and each portion 214a, 214b can include any number of slits. In some embodiments, the slits 216a, 216b are configured such that certain portions of the elongate tubular body 212 between the slits 216a, 216b can extend outward away from a central axis A of the tubular body 212 when the body 212 is axially rotated and/or compressed. As a result of the portions 214a, 214b extending outward, one or more wings can form in each of the proximal and distal portions 214a, 214b to engage tissue therebetween.

In an exemplary embodiment, as shown in FIG. 2, the slits 216a, 216b are substantially S-shaped. The slits 216a, 216b can extend longitudinally along the elongate tubular body 212 in a proximal-distal direction, and they can be spaced axially around the elongate tubular body 212. In some embodiments, the slits 216b in the distal portion 214b can extend in a first direction around a circumference of the elongate tubular body 212 and the slits 216a in the proximal portion 214a can extend in a second, opposite direction around the circumference of the elongate tubular body 212. Such a configuration can allow the tubular body 212 to be rotated in a first direction to cause only one of the proximal and distal portions 214a, 214b to radially expand, and then to be rotated in a second direction to cause the other one of the proximal and distal portions 214a, 214b to radially expand.

In the pre-deployed configuration of the implant 202 shown in FIG. 2, the elongate tubular body 212 has a diameter such that it is configured to fit within a lumen, or opening, in tissue, e.g., through a lumen of the stomach and/or in the intestine. The tubular body 212 is also configured to fit within an introducer sheath or other instrument for inserting into a body and guiding the device 100.

As shown in FIG. 2, the implant 202 can include a conical guide portion 210, extending from the distal end 205b of the body 212. A distal tip 220, which can be configured as a needle point or similar sharp feature, can extend distally from a distal end 211 of the guide portion 210. The distal tip 220 can be used to puncture tissue to create an opening for inserting the implant 202 therein, and the guide portion 210 can be distally tapered to facilitate insertion of the implant 202 into the tissue punctured by the distal tip 220.

In some embodiments, the distal tip 220 can include suitable surface features that facilitate its use for puncturing tissue. For example, the distal tip 220 can have a helical thread extending across a portion or a majority of the distal tip 220. The distal tip 220 can be attached to the guide portion 210 at the distal end 206b of the implant 202. The distal tip 220 can be coupled to one or more components disposed within the tubular body 212 (not shown). In some embodiments, the distal tip 220 can be configured as or can be part of an occlusion member that can preclude fluids from flowing through the tubular body 212, for example, as described in the U.S. Patent Application Publication No. 2013/0165963, entitled "Devices and Methods for Occluding or Promoting Fluid Flow," filed Dec. 21, 2011, the content of which is incorporated herein by reference in its entirety.

Figure 3:
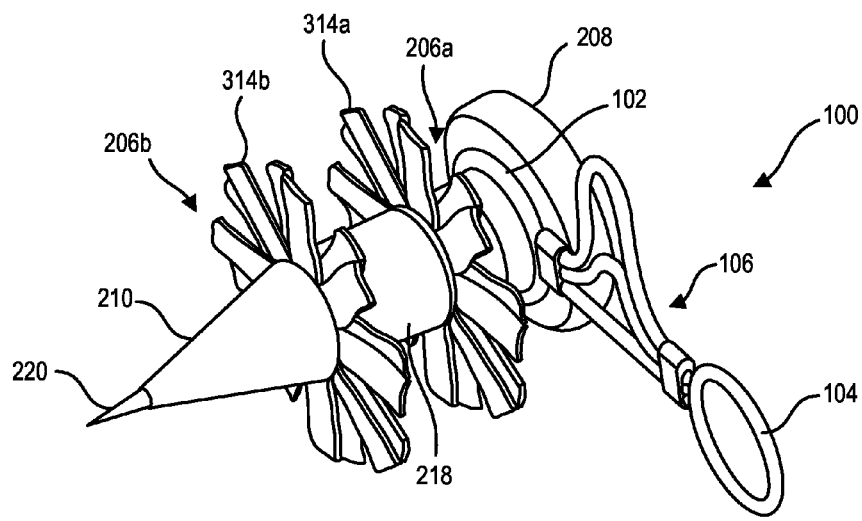
FIG. 3 is a perspective side view of the assembly of FIG. 2 with deployable wings of the first implant being deployed.

After the implant 202 is inserted into tissue at the implantation site, the proximal and distal portions 214a, 214b can be expanded to form proximal and distal wings 314a, 314b shown in FIG. 3. In the embodiments shown in FIGS. 2-6, the slits 216a, 216b can be configured such that the proximal and distal portions 214a, 214b each form two sets of wings. In one embodiment, the proximal and distal portions 214a, 214b each form two sets of eight wings. It should be appreciated, however, that the proximal and distal portions of the implant in accordance with some embodiments can be configured to form any number of wings, which can be aligned or radially offset from each other, as the described embodiments are not limited in this respect.

FIG. 3 shows that, in the deployed configuration, the proximal portion 214a of the implant 202 is expanded to form proximal wings 314a, and the distal portion 214b is expanded to form distal wings 314b. The wings 314a, 314b are formed by the material between the slits 216a, 216b, which is deformed outward as the outer elongate body 212 is rotated and/or compressed. The wings 314a, 314b can be concurrently or sequentially formed, e.g., by deploying the distal wings 314b before the proximal wings 314a. However, in some embodiments, the proximal wings 314a can be formed prior to forming the distal wings 314b.

The wings 314a, 314b on the implant 202 can be formed by rotating and/or compressing the device 202. While various techniques can be used to deploy and actuate the device 202, in one exemplary embodiment, the implant 202 can be removably coupled to an actuator that can be adapted to guide the implant 202 into a body and to apply an axial and rotational force to the elongate tubular body 212 to cause portions of the elongate tubular body 212 to extend outwardly. FIG. 2 shows that the guide member 204 can be coupled to a shaft 209 of an actuator (not shown). In one embodiment, the proximal and distal wings 314a, 314b can include tissue engaging mechanisms that grasp tissue as the wings are formed. The wings 314a, 314b can be formed by, for example, compressing the proximal and distal portions 214a, 214b as they are rotated to form the wings.

The tubular body 212 can be formed from a variety of materials including absorbable and non-absorbable materials. In an exemplary embodiment, the implant 202 is formed from a deformable material that undergoes plastic deformation (i.e., deformation with negligible elastic component). Exemplary materials include, by way of non-limiting examples, any resorbable (e.g., biocompatible and/or bioabsorbable) materials, including, for example, titanium (and titanium alloys), magnesium alloys, stainless steel, polymeric materials (synthetic and/or natural), shape memory material such as Nitinol®, ceramic, etc. Materials which are not normally radiopaque, e.g., magnesium alloy, may be enhanced and made x-ray visible with the addition of x-ray visible materials, such as particles of iron oxide, stainless steel, titanium, tantalum, platinum, or any other suitable equivalents. In some embodiments, other materials including non-permeable materials, such as polyethylene terephthalate and polyvinylidene chloride, and semi-permeable materials, such as polylactide, can additionally or alternatively also be used to form and/or coat the tubular body 212.

In use, the device 100 having the implant 202 in a pre-deployed configuration attached thereto, as shown in FIG. 2, can be endoscopically or laparoscopically inserted in the patient's body. For example, a delivery system having the guide member 204 at a proximal end of the shaft 209 (FIG. 2) can be used to deliver the device 100 engaged with the implant 202 into the implantation side. It should be appreciated, however, that the device 100 and the implant 202 can be delivered to the implantation site in any suitable manner. The device 100 can be coupled to the implant 202 or, alternatively, in some cases, the device 100 and the implant 202 can be delivered to the implantation site separately.

Figure 13:
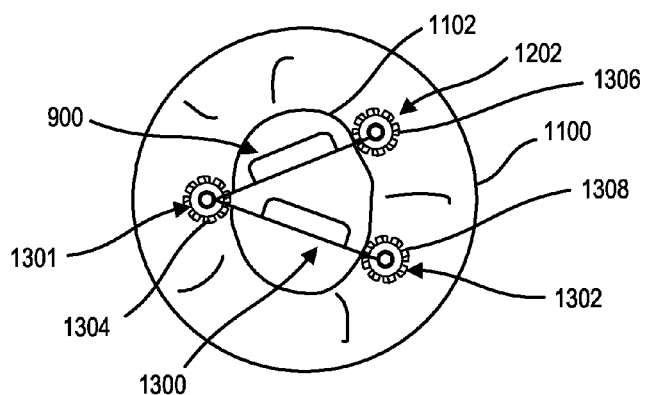
FIG. 13 is a schematic illustration of another embodiment of a method of controlling a size of a pylorus.

Although not shown in FIGS. 2-6, in some embodiments, a first or primary deployable implant used to anchor a device, such as the device 100, to tissue, can be used to anchor more than one of such devices to tissue. For example, the first deployable implant 202 can be passed through more than one attachment member, such as a loop similar to the loop 102 in FIG. 2 or another type of the attachment member(s) of a device, to thus mate the devices including those attachment members to the implant 202. In the embodiment illustrated in FIG. 2, more than one loop can be placed over the proximal end 205a of the tubular body 212 against the collar 208. In this way, when the first implant 202 is deployed, more than one device (e.g., two, three or more) is anchored to tissue. Each of the devices anchored using the same primary implant can be used to restrict a size of a pyloric orifice. For example, the devices can be positioned so as to at least partially extend across the pyloric orifice and each of the devices can be affixed at a respective different location in the vicinity of the pyloric opening using a respective second or secondary implant. The secondary implants can be affixed to tissue on the opposite side of a location at which the primary implant is affixed. Exemplary embodiments of a method of using the same first implant to anchor more than one device to tissue are shown in FIG. 13.

As discussed above, the described techniques can be particularly useful for controlling a size of a pylorus. Accordingly, in some embodiments, the implant 202 with the device 100 can be delivered to the pyloric opening. Once the implant 202 is brought in proximity to the pyloric opening, the tip 220 of the implant 202 can be used to puncture tissue at one side of the pylorus. After an opening in the tissue is thereby created and the implant 202 is positioned at the desired location, the implant 202 can be manipulated to cause the proximal and distal portions 214a, 214b of the tubular body 212 to expand, such that the proximal and distal wings 314a, 314b wings are deployed to engage tissue therebetween. In the embodiment of FIG. 3, the proximal portion 214a is configured to form two sets of wings which are radially offset with respect to each other. Similarly, the distal portion 214b is configured to form two sets of wings which are radially offset with respect to each other. The proximal and distal wings 314a, 314b can be aligned with respect to each other, as shown in FIG. 3.

In some embodiments, the distal wings 314b can be deployed prior to deploying the proximal wings 314a. After the puncture is created on one side of the tissue wall of the pylorus opening and the implant 202 is positioned such that the mid-portion 218 traverses the puncture and the proximal and distal portions 214a, 214b are disposed at the opposite sides of the tissue wall, the implant 202 can be manipulated to cause the distal portion 214b to expand to form the distal wings 314b on one side of the tissue wall. After the distal wings 314b are deployed, the implant 202 can be manipulated to cause the proximal portion 214a to expand to form the proximal wings 314a on the opposite side of the tissue wall. However, in some embodiments, the proximal wings 314a can be deployed before the distal wings 314b are deployed. Additionally or alternatively, the proximal and distal wings 314a, 314b can be formed simultaneously or at least partially simultaneously, such that at least a portion of a time period during which the distal wings 314b are formed overlaps with a time period during which the proximal wings 314a are formed.

Regardless of the manner in which the proximal and distal wings 314a, 314b are formed and of the order of deployment of the wings, as a result of the wing formation, the implant 202 anchors the device 100 to tissue at a body orifice, such as the pyloric opening. The implant 202, as well as other implant devices that can be employed in the described techniques, can be implanted into tissue in the vicinity of the pylorus and/or into tissue of the stomach wall.

After the full deployment of the implant 202, an actuator (not shown) proximally coupled to the guide member 204 can be separated from the implant 202 and removed from the surgical site, as shown in FIG. 3. As a result, the implant 202 remains affixed into tissue while being engaged with the device 100.

Figure 4:
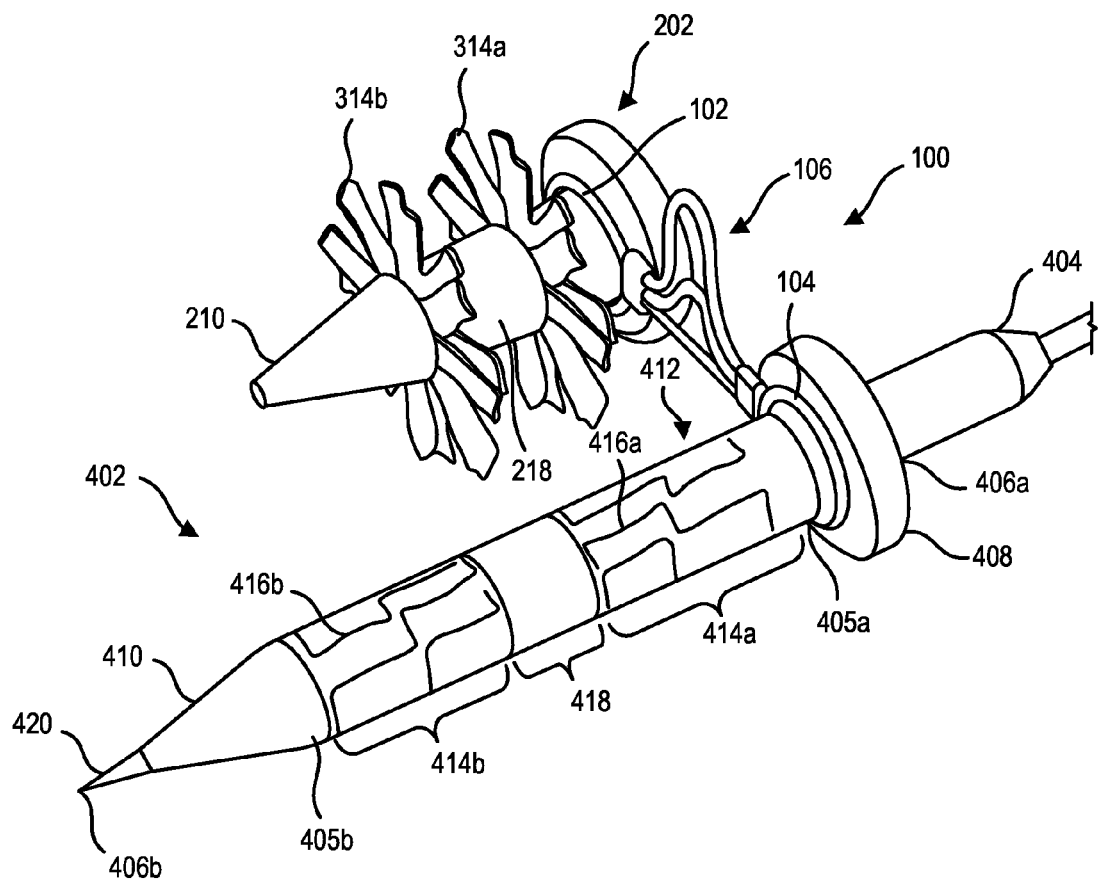
FIG. 4 is a perspective side view of the device of FIG. 3 including a second deployable implant attached thereto, prior to deployment of the second implant.

Referring back to FIG. 2, in an undeployed configuration of the implant 202, the tip 220 can protrude distally from the guide portion 210. In some embodiments, after the implant 202 is injected into the implantation site, either before or after the proximal and distal portions 214a, 214b are expanded to form proximal and distal wings 314a, 314b to engage tissue therebetween, the tip 220 can be retracted into the body of the deployed implant 202. FIG. 4 illustrates the implant 202 having the tip 220 retracted into the body of the implant. In this way, the possibility of damaging tissue at the implantation site with the end of the tip 220 can be eliminated.

FIG. 4 shows the implant 202 having the proximal and distal wings 314a, 314b fully deployed and being attached to the device 100 via the attachment member 102. After the implant 202 is affixed into the tissue on one side of the pyloric opening, another, second, implant 402 in an undeployed configuration can also be attached to the device 100, e.g., via the second attachment member 104, as shown in FIG. 4. The second attachment member 104 can be shaped as a loop, similar to first attachment member 102, however, other configurations can be utilized as well. As shown in FIG. 4, the second implant 402 can be similar to the first implant 202 and can be passed with its distal tip 420 through the second attachment member 104.

Figure 5:
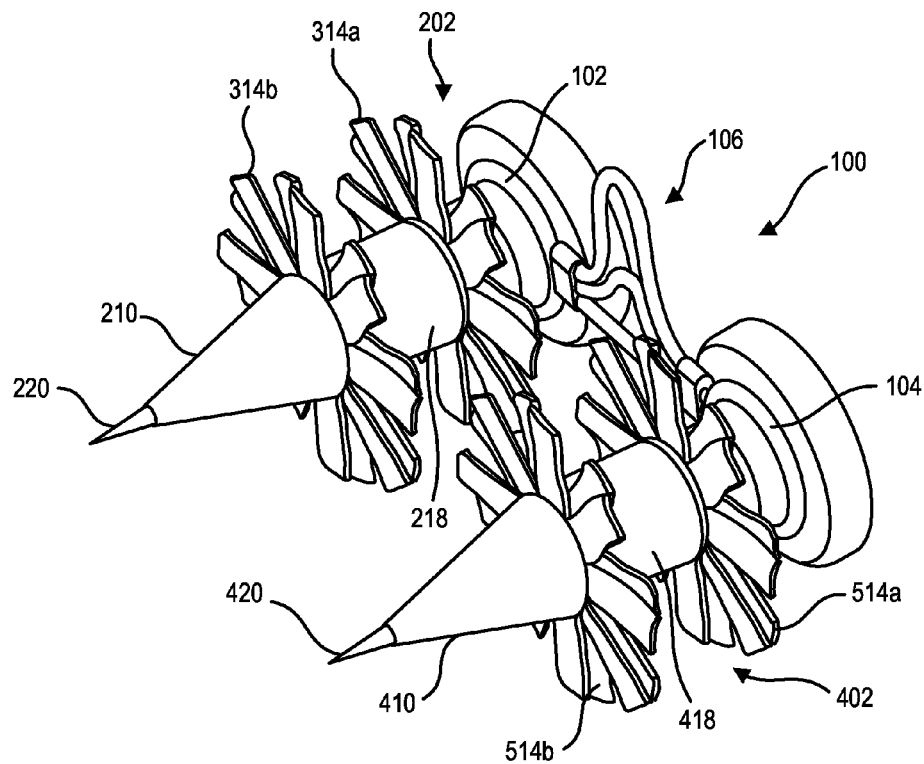
FIG. 5 is a perspective side view of the device of FIG. 4 with both the first and second implants being deployed.

Like the first implant 202, the second implant 402 can have an elongate tubular body 412 having proximal and distal ends 405a, 405b. As shown in FIG. 5, the elongate tubular body 412 can include proximal and distal portions 414a, 414b having proximal and distal slits 416a, 416b, respectively, and a mid-portion 418. A distally tapered guide portion 410 can extend from the distal end 405b of the tubular body 412, and a distal tip 420 can extend distally from the guide portion 410. A collar 408 can be disposed at the proximal end 405a of the tubular body 412 and used as a stop to prevent the attachment member 104 from sliding proximally off the implant 402. The guide member 404, which can be a part of a delivery tool assembly configured to deliver the implant 402 to the surgical site, can be coupled to the proximal end 406a of the second implant 402. The proximal and distal portions 414a, 414b can be configured to expand to form respective proximal and distal wings that engage tissue therebetween.

In use, after the implant 402 is received by the attachment member 104 of the device 100, tension can be applied to the device 100 to cause the pyloric opening (or other body orifice a size of which is being controlled) to reduce in size. An actuator, or any other suitable device attached to the guide member 404 removably coupled to the proximal end 406a of the device 402 (FIG. 4), can be used to move the implant 402 in the direction along the diameter of the pyloric opening, such that the device 100 engaged with the implant 402 is pulled across the opening to reduce its size. In other words, the second implant 402 is moved away from the first implant 202 so that the second implant 402 can be anchored in tissue on an opposite side of the pylorus than the first implant 202. One or more components of the device 100 (e.g., the connector 106 and/or other components) can be made from an elastic material so that the device 100 can be stretched as it is pulled to narrow the opening.

After the desired position of the device 100 is achieved, and while the device 100 is being tensioned, the implant 402 can be used to pierce tissue on the side of the pyloric opening that is opposite to the side where the implant 202 has been deployed. The implant 402 can then be deployed such that the proximal and distal portions 414a, 414b are expanded to form proximal and distal wings 514a, 514b shown in FIG. 5, which can be done similarly to the deployment of the wings 314a, 314b. When the device 100 is being manipulated by a suitable grasper device coupled to the implant 402, the device 100 can be moved such that tissue around the pyloric aperture and/or in proximity to the pyloric aperture is folded or plicated, or manipulated in other ways to decrease a size of the pyloric opening.

After the full deployment of the implant 402, an actuator (not shown) coupled to a proximal end of the guide member 404, as well as the guide member 404, can be separated from the implant 402 and removed from the surgical site, as also shown in FIG. 5. It should be noted that, even though the distal tips 220, 420 are shown in FIG. 5, the tips 220, 420 can be retracted (e.g., as shown for the implant 202 in FIG. 4) after they are used to penetrate tissue, so as to avoid protruding sharp edges that can potentially damage the tissue. This can be particularly useful for decreasing trauma to sensitive tissue in the gastrointestinal tract.

As a result of the deployment of the second implant 402 following the deployment of the first implant 202, the device 100 will be positioned at the pyloric opening such that connector 106 extends across the opening and between the first and second implants 202, 402. The implants 202, 402 thus affix the device 100 into the tissue on the respective opposite sides of the opening. In this way, the natural size of the pyloric aperture is reversibly decreased and a desired size of the opening can be maintained by virtue of the connector 106 of the device 100. The pyloric opening can be maintained in a partially open state for any duration of time and can be returned to a fully open state when desired.

It should be appreciated that the deployable implants 202, 402 are not necessarily implanted into tissue at respective opposite sides of the pyloric opening. To control an opening size of the pylorus, the deployable implants 202, 402 (or any other deployable implants can be used for the same purpose) can be implanted at any suitable respective locations in the vicinity of the pyloric opening.

Figure 6:
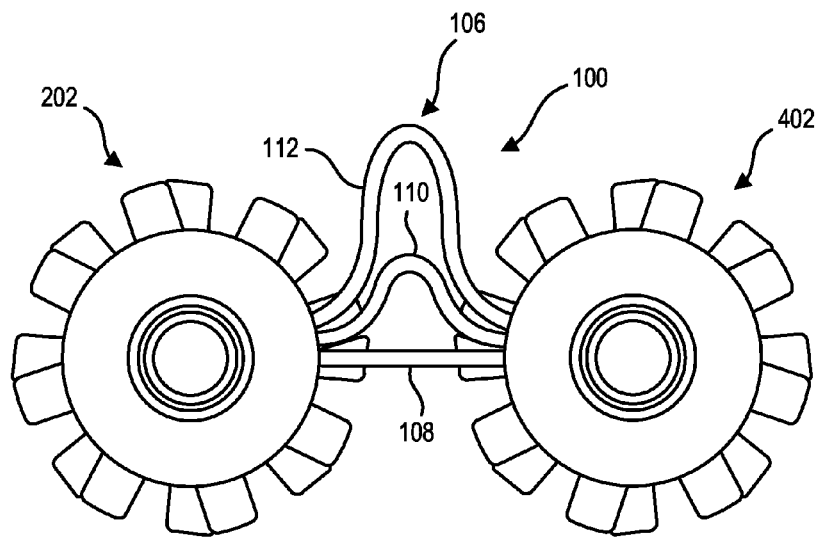
FIG. 6 is a rear view of the device of FIG. 5.

FIG. 6 shows a rear view of the device 100 when at least one of the proximal and distal wings 314a, 314b of the first implant 202 are deployed and at least one of the proximal and distal wings 514a, 514b of the second implant 402 are deployed. When the proximal portion 214a of the first implant 202 is radially expanded to form the proximal wings 314a, the proximal wings 314a can be aligned with the distal wings 314b to facilitate attachment to tissue. Similarly, the proximal wings 514a of the second implant 402 can be aligned with the distal wings 514b as shown in the example of FIG. 6. It should be appreciated, however, that, in some embodiments, proximal and distal wings of an implant can be radially offset with respect to each other.

Furthermore, it should be appreciated that, even though essentially identical implants 202 and 402 are shown to be coupled to the device 100 in FIGS. 4-6, the implants 202, 402 can have different configurations. Any type of a deployable device configured to be received by the attachment members of the device 100 and to be implanted into tissue to hold the device 100 in place can be utilized additionally or alternatively, as embodiments are not limited in this respect. The implants 202, 402 can be configured to form any suitable number of wings, which can be the same or different among the implants, and proximal and distal wings can be aligned or offset with respect to each other. In addition, the attachment member 102 is shown to first receive the implant 202 by way of example only, as the attachment member 104 can alternatively be used as a primary implant to anchor the device 100 to tissue.

After the implants 202, 402 are deployed, the device 100 can remain at the surgical site by virtue of it being coupled to the implants 202, 402 via the attachment members 102, 104, as shown in FIG. 5. The implants 202, 402 can be deployed within tissue at different locations in proximity to the orifice such that the connector 106 of the device 100 at least in part traverses the constricted orifice. The connector 106 will thus set a diameter of the orifice. However, in some cases, depending on the manner in which the device 100 is disposed within the body, the connector 106 can be positioned such that it does not traverse the orifice.

As discussed above, the portions 108, 110, 112 of the connector 106 can be configured such that the length of the longest third portion 112 is smaller than the size (e.g., a diameter or other dimension) of the orifice a size of which can be controlled using the device 100. It should be appreciated that the three portions 108, 110, 112 are shown by way of example only, as the connector 106 can include any suitable number of portions of different lengths (e.g., two, four, five, etc.), which can be used to decrease and then to sequentially (or in other manner) increase the size of the body orifice. If it is no longer desirable to restrict the size of the body orifice (e.g., when the obesity treatment has been successful and desirable weight loss is achieved, or in any other circumstances), all of the portions 108, 110, 112, or any remaining portions of the connector 106 that have not been yet cut, can be cut or otherwise broken so that the orifice reverts to its natural size and no restrictions are imposed thereon.

Figure 7:
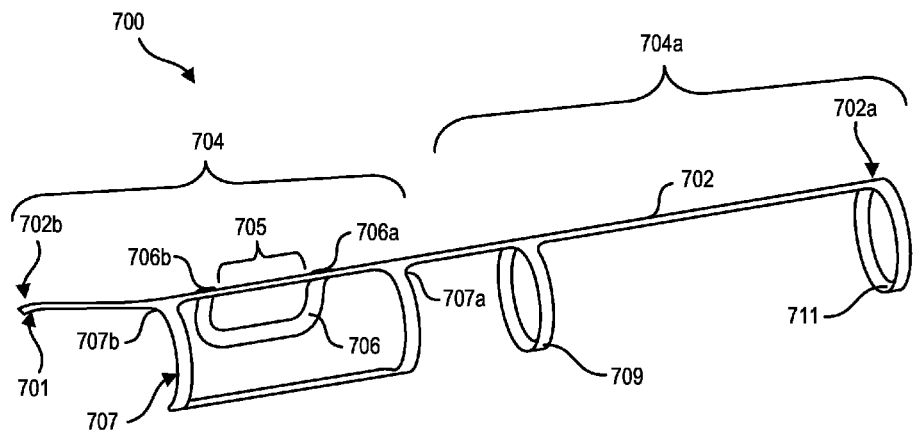
FIG. 7 is a side perspective view of a device in accordance with another embodiment.
Figure 8:
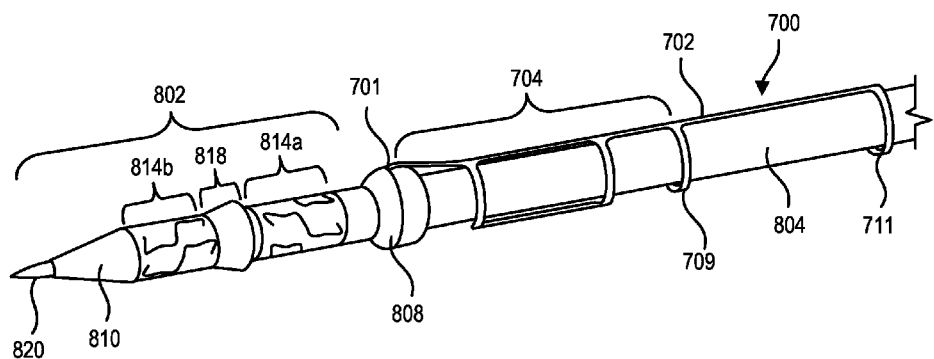
FIG. 8 is a side perspective view of the device of FIG. 7 having one embodiment of a first deployable implant and an actuator tool attached thereto, prior to deployment of the first implant.

FIGS. 7 and 8 illustrate another embodiment of a device 700 that can be used to control a size of a body orifice, such as a pyloric opening. The device 700 can be configured to mate to first and second implants which, in some embodiments, can be similar to the first and second implants 202, 402 discussed above. FIG. 8 shows such a first deployable implant 802 that can be engaged with the device 700. The device 700 can be shaped to mount on and wrap around a delivery tool assembly including the first implant 802.

As shown in FIGS. 7 and 8, the device 700 generally includes an elongate spine 702 having proximal and distal ends 702a, 702b. At least one attachment member is formed on or coupled to the spine 702 for mating the device to an implant. In the illustrated embodiment, the distal end 702b forms a first attachment member 701 that is configured to directly mate to a first implant, and the device 700 includes a second attachment member 709 for mating to a second implant. The first and second attachment members 701, 709 define a connector portion 704 extending therebetween for maintaining a distance between first and second implants coupled to the attachment members 701, 709. The connector portion 704 can include bridge portions for allowing a distance between the implants to be adjusted. The device can also include a third attachment member 711, which is shown located at the proximal end 702a of the spine 702, for coupling to a third implant, as will be discussed in detail below.

The attachment members 701, 709, 711 can have a variety of configurations. In the illustrated embodiment, the first attachment member 701 is merely the terminal distal end 702b of the spine 702, and it can be configured to mate directly to an implant, e.g., using an adhesive or other attachment technique known in the art. However, the attachment member 701 can alternatively be in the form of a loop or other member for coupling to and engaging an implant. The second and third attachment members 709, 711 can also have a variety of configurations, but are shown as a ring or loop that can removably and slidably receive a respective deployable implant. The second and third attachment members 709, 711 can also be configured to receive a delivery tool therethrough, as shown in FIG. 8, for allowing the delivery tool to be used to deliver the implant with the device 700 mounted thereon. The loop can be formed from various materials and can have varying degrees of flexibility/rigidity and/or elasticity. It should be appreciated that the attachment members can have any other configuration.

The connector portion 704 can also have various configurations. In the illustrated embodiment, the connector portion 704 has multiple brackets located between the attachment members 701, 709 and having different lengths. In particular, the connector portion 704 includes a short bracket 706 and a long bracket 707 formed along the spine 702. However the device can include any number of brackets. The brackets are preferably arranged to straddle one another, with each bracket increasing in size as compared to the bracket disposed therebetween. In particular, each bracket can have a generally U-shaped configuration with opposed ends that couple to the spine 702. As shown, the short bracket 706 includes first and second ends 706a, 706b that are coupled to the spine 702, and the long bracket 707 similarly includes first and second ends 707a, 707b that are connected to the spine 702. The first and second ends 706a, 706b of the short bracket 706 are coupled to the spine at respective locations between the first and second ends 707a, 707b of the long bracket 707. As a result, the brackets 706, 707 are coupled to the spine 702 so as to form three bridge portions of the connector 704. In particular, a first bridge portion 705 of the spine 702 is formed between the first and second ends 706a, 706b of the short bracket 706, and the first bridge portion 705 has a first length. The short bracket 706 defines a second bridge portion having a second length that is equal to the length of the second bridge portion as measured along the bridge portion between the ends 706a, 706b. The long bracket 707 defines a third bridge portion having a third length that is equal to the length of the third bridge portion as measured along the bridge portion between the ends 707a, 707b. The first bridge portion 705 is thus the shortest, the second bridge portion (i.e., bracket 706) is longer than the first bridge portion 705, and the third bridge portion (i.e., bracket 707) is the longest among the portions.

The brackets 706, 707 can be formed integrally with the spine 702 or they can be attached to the spine 702 in any suitable manner. The brackets 706, 707 can extend in opposite directions from the spine 702, as shown, or they can both be positioned on the same side of the spine. In the illustrated embodiment, the brackets 706, 707 each have a U-shaped or semicircular configuration. One skilled in the art will appreciate, however, that the brackets 706, 707 can have any size and/or shape so as to form bridge portions of the connector 704 having multiple lengths. Furthermore, the device 700 can include more than two brackets and/or elements having any other sizes and shapes that can form any suitable number of bridge portions.

As indicated above, the device 700 can include a third attachment member 711 located at the proximal-most end 702a of the spine 702. In some embodiments, rather than using the second attachment member 709, the third attachment member 711 can alternatively be used to mate to a second deployable implant. In such embodiments, the device 700 can be considered to have a connector portion 704a that extends from the first attachment member 701 to the third attachment member 711. Thus, the third attachment member 711 can be mated to the second deployable implant, for example, when it is desirable to reduce a size of a larger opening (or a larger portion of an opening) such that the length of the connector 704 may not be sufficient to span the opening even when its size is reduced. As another scenario, the third attachment member 711 can be used when an opening is to be restricted to a lesser degree using connector 704A as compared to a case when the opposite sides of the opening are brought closer together using connector 704. Although not shown in FIGS. 7 and 8, the device 700 can include only one (e.g., 709 or 711) or more than two attachment members and different attachment members can be utilized to mate to a second implant in different contexts.

It should be appreciated that the device 700 can have a suitable number of any features coupled to the spine 702 and having any suitable configuration and size. For example, as one variation, the device 700 can include only one of the brackets 706, 707. As another variation, the device 700 can include one or more brackets having a closed circular cross-section which can have cut-outs of any suitable shapes. The size, configuration, and number of the features can be selected such that the size of the pyloric opening can be controlled to be gradually increased, according to patient's conditions, a progress of weight loss, and any other factors.

In use, the connector portion 704 of the device 700 can be configured to function as a bridge that holds the attachment members 701, 709 at a predetermined distance apart. The connector 704 is shown to include three bridge portions, i.e., the first bridge portion 705, the short bracket 706 hereinafter also referred to as the second bridge portion 706, and the long bracket 707 hereinafter also referred to as the third bridge portion 707. When the device 700 is implanted to restrict a size of the pyloric opening and when the first, second, and third bridge portions 705, 706, 707 are intact, the initial, first distance between the attachment members 701, 709 mated to the first and second implants, respectively, will depend on (e.g., be equal to) the length of the shortest, first bridge 705 portion.

If a subsequent increase of the opening is desired, one or more of the brackets can be sequentially or simultaneously cut, broken, removed, or otherwise altered to change a distance between the attachment members 701, 709. For example, the first bridge portion 705 can be cut anywhere along its length so as to free the first and second ends 706a, 706b of the short bracket 706, allowing the ends 706a, 706b to move apart. As a result, a distance between the attachment members 701, 709 will move from a first distance, as maintained by the first bridge portion 705, to a second larger distance as determined by the second bridge portion 706. If a further increase in the size of the pyloric opening is desired, the short bracket 706 can also be cut anywhere along its length so as to free the first and second ends 707a, 707b of the long bracket 707, allowing the ends 707a, 707b to move farther apart. As a result, the distance between the attachment members 701, 709 will move from the second distance, as maintained by the second bridge portion 706, to a third larger distance as determined by the third bridge portion 707. If no reduction in size of the pyloric aperture is desired, the large bracket 707 can be cut as well such that the device 700 no longer maintains the implants at a distance apart from one another, and the pyloric opening thus becomes fully open. The cut portion(s) may then optionally be removed from the implantation site.

As indicated above, the device 700 can be used in conjunction with a delivery tool assembly for delivering an implant. FIG. 8 illustrates a first implant 802 that can be delivered to an implantation site using a delivery assembly including an elongate tubular guide member or shaft 804 having the first implant 802 removably attached to a distal end thereof. In some embodiments, the device 700 can be configured such that it conforms to the size and shape of the elongate tubular guide member 804. Thus, as shown in FIG. 8, the attachment members 709, 711 of the device 700 can be configured to receive the guide member 804 therein, which allows the implant 802 to be delivered through a minimally invasive portal without interference from the device 700.

As discussed above, the first implant 802 can be coupled to the device 700 by mating to the first attachment member 701 at the distal end 702b of the device 700. The first implant 802 can be configured similarly to the first and second implants 202, 402 described above and can have an elongate tubular body including proximal and distal portions 814a, 814b and a mid-portion 818. The proximal and distal portions 814a, 814b can be configured to expand to form respective proximal and distal wings (not shown) that engage tissue therebetween, as described above. A distally tapered guide portion 810 can extend from a distal end of the tubular body, and a distal tip 820 can extend distally from the guide portion 810. As shown in FIG. 8, a collar 808 can be disposed at a proximal end of the tubular body and can have the first attachment member 701 fixedly mated thereto. The attachment member 701 at the distal end 702b of the device 700 can be glued, welded, or otherwise attached to the first implant 802. It should be appreciated that the first implant 802 can be mated to the device 700 in any other suitable manner, including using an attachment member of a different type.

In use, the first implant 802 with the device 700 can be delivered to the implantation site in an undeployed configuration. To deliver the first implant 802 to the implantation site, e.g., into tissue of the pylorus, the distal tip 820 can be used to pierce tissue at that site. After the first implant 802 is properly positioned at the implantation site, an actuator, which can be included in the delivery tool assembly or which can be a separate suitable instrument, can be used to manipulate the first implant 802 to cause the proximal and distal portions 814a, 814b to expand so as to form proximal and distal wings. After the wings are formed, which can be done similarly to that described above for the implants 202 and 402, the guide member or shaft 804 can be separated from the first implant 802 such that the first implant 802 is ejected from the delivery assembly. In the example illustrated, the shaft 804 can slide out of attachment members 709, 711.

After the first implant 802 is deployed, a second implant (not shown) can be passed through one of the attachment members 709, 711 of the device 700 and used to place the device 700 at a proper position for controlling a size of a body orifice. The second implant can be similar to any of implants 202, 402, and 802, or it can be a different device configured to be affixed into tissue. In some embodiments, the second implant can be inserted through the second attachment member 709 and it can remain engaged with that implant after the implant is deployed into tissue around the body orifice. However, the second implant can alternatively be passed through the third attachment member 711 or any other feature that can be formed on the device 700. For example, in some embodiments, more than two attachment members coupled to the spine 702 can be formed proximally of the brackets 706, 707.

As discussed above, different attachment members can be selectively used to mate the device 700 to the second implant, based on a position of the device 700 with respect to the pyloric opening, a desired degree of restriction of the pyloric orifice, a size of the pyloric orifice, and/or any other factors. For example, if the device 700 is positioned so as to span a diameter (or a widest part) of the pyloric opening, the second implant can be passed through the third attachment member 711 which is disposed farthest away from the first attachment member 701 mated to the first implant 802. Alternatively, if the device 700 is to be implanted so that it is offset from the diameter (or the widest part) of the pyloric opening, the second implant can be mated to the device 700 using the second attachment member 709 which is closer to the first implant 802. Accordingly, multiple features of the device 700 can allow flexibility in positioning of the device 700 and can permit narrowing the pyloric opening to different degrees.

When both the first implant 802 (FIG. 8) and the second implant not shown herein are fully deployed, a portion of the device 700, for example, the connector portion 704 extending between the attachment members 701, 709 mated to the first and second implants, respectively, can be used to control a size of the pyloric opening. In some embodiments, as discussed above, the bridge portions 705, 706, 707 of the connector 704 can be cut, broken, removed, or otherwise altered to increase the size of the pyloric opening after it has been initially restricted using the device 700 in an intact form. This can be done when the implants and device are initially implanted, or during one or more subsequent procedures in which it is desired to adjust a size of the pylorus.

The device 700 can be made from a material that can withstand contractions of the stomach as food is forced into the small intestine, and can be adjustable to control a diameter of the pyloric aperture. Exemplary materials can include the same materials as the materials described above that are used to make the device 100, or any other materials.

Figure 9:
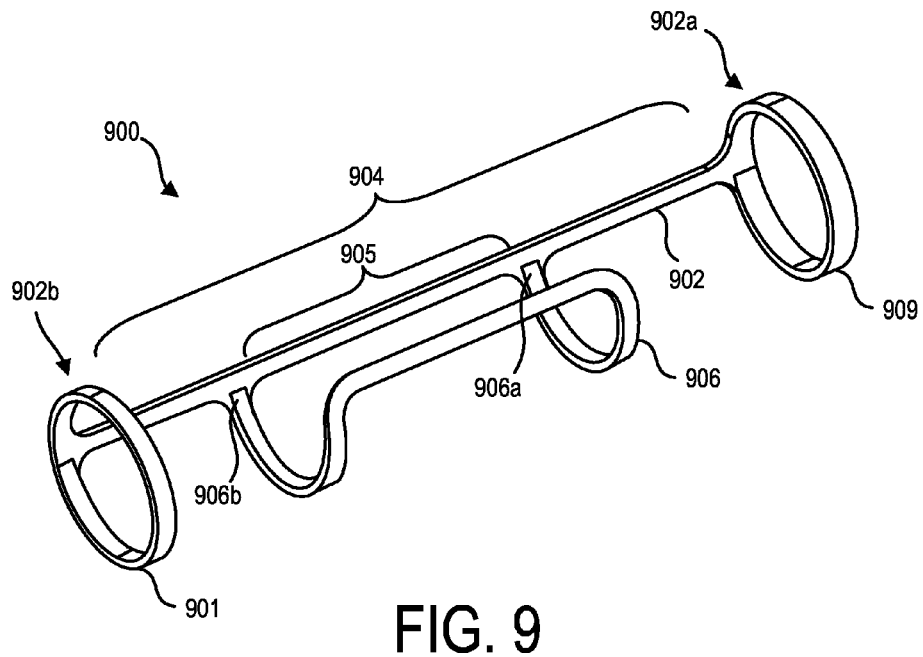
FIG. 9 is a side perspective view of a device in accordance with another embodiment.

FIG. 9 illustrates another embodiment of a device 900 that can be used to control a size of a body orifice, such as a pyloric opening. Similar to the device 700 of FIGS. 7 and 8, device 900 can be configured to conform to a size and shape of a delivery assembly used to deliver a first deployable implant to tissue. The device 900 can be mounted on the delivery assembly (not shown) and can be anchored into tissue using the first deployable implant.

As shown in FIG. 9, the device 900 can include first and second attachment members 901, 909, a spine 902 extending between the first and second attachment members 901, 909, and a bracket 906 having first and second ends 906a, 906b coupled to the spine 902. In the illustrated embodiment, the bracket 906 is semicircular or U-shaped, however it can have any other shape. By way of a non-limiting example, the attachment members 901, 909 can be configured as loops and can be positioned at opposite sides of the bracket 906. As shown in FIG. 9, the bracket 906 is disposed at a mid-portion of the spine 902, the first attachment member 901 is located at a distal-most end 902b of the device spine 902, and the second attachment member 909 is located at a proximal-most end 902a of the device 900.

In the illustrated embodiment, the spine 902 of the device 900 can form a connector 904 used to control a distance between the attachment members 901, 909 after the device 900 is affixed to tissue in the vicinity of the pyloric opening. The connector functions similar to the connector described above with respect to FIGS. 7 and 8, but only includes the single bracket 906. In particular, a portion of the spine 902 extending between first and second ends 906a, 906b of the bracket 906 can form a first bridge portion 905 that maintains the first and second attachment members 901, 909 at a first distance apart. When the first bridge portion 905 is cut, the first and second ends 906a, 906b of the bracket 906 can move apart, and the bracket 906 can define a second bridge portion that maintains the first and second attachment members 901, 909 at a second distance apart that is greater than the first distance.

In use, the first and second attachment members 901, 911 can each mate with a respective deployable implant (e.g., any of the implants 202, 402, 802 discussed above) such that, when the implant is deployed, the device 900 is anchored to tissue at the vicinity of a body orifice, such as a pyloric opening. The device 900 can be positioned at the pyloric opening such that the connector 904 is at least partially positioned across the opening. One skilled in the art will appreciate that the orientation of the device 900 can be reversed such that distal-most end 902b of the device 900 becomes the proximal-most end 902a, as the described embodiments are not limited to a specific orientation and position in which the device 900 can be anchored into tissue.

After the deployable implants with the device 900 are deployed to affix to tissue at the pyloric opening, the distance between the attachment members 901, 909 can initially depend on a length of the spine 902 extending between the attachment members 901, 909. The connector 904 of the device 900 can then be used to adjust the size of the pyloric orifice. For example, after the size of the pyloric opening is initially restricted by the device 900 in its intact form, if desired, the first bridge portion 905 can be cut to increase the size of the opening so that the distance between the attachment members 901, 909 increases and becomes dependent on the length of the second bridge portion, which is equivalent to the bracket 906. If a further increase in the size of the opening is desired, it can be widened by cutting the bracket 906 as well, such that the size of the opening becomes unrestricted.

One skilled in the art will appreciate that the device 900 can include more than one bracket (e.g., two, three, four or more) so that the device 900 can be cut once, twice, or more than twice to thus adjust a size of a body orifice in multiple steps. For example, similar to device 700 (FIG. 7), the device 900 can include more than one bracket having any longitudinal length and positioned in any manner along the spine 902. In addition, the device 900 can include any other features of any size and configuration that facilitate delivery of the device 900 to the implantation site and allow using it in different patients and for different conditions.

Figure 10:
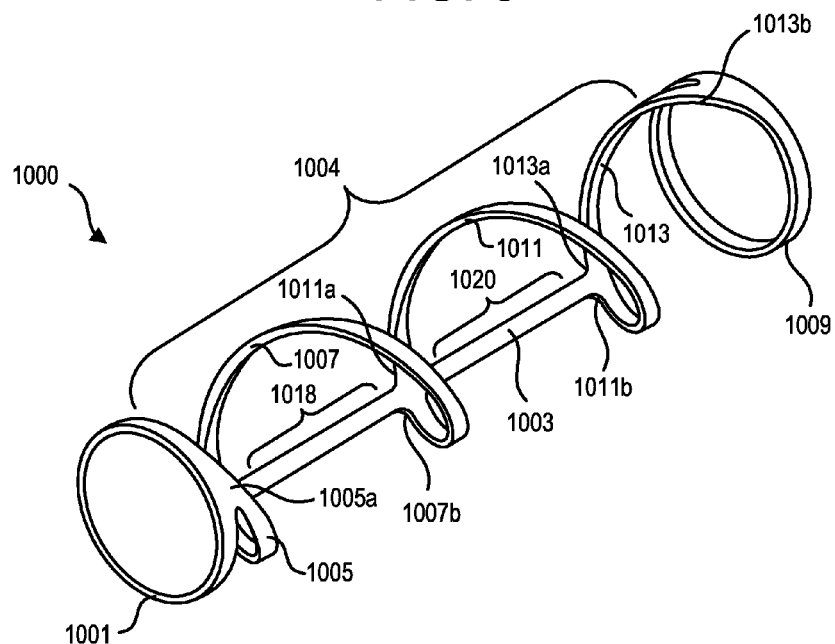
FIG. 10 is a side perspective view of a device in accordance with another embodiment.

FIG. 10 illustrates another exemplary embodiment of a device 1000 that can be used to control a size of a body orifice, such as a pyloric opening. Similar to the device 700 (FIGS. 7 and 8) and the device 900 (FIG. 9), the device 1000 is configured to conform to a size and shape of a delivery assembly used to deliver a first deployable implant to an implantation site. To deliver the device 1000 to the implantation site, it can be mated to the first implant and mounted on the delivery assembly coupled to a proximal end of the first implant.

As shown in FIG. 10, the device 1000 can include first and second attachment members 1001, 1009, and a connector 1004 extending between the first and second attachment members 1001, 1009. The connector 1004 can include a straight spine 1003 and arcuate first, second, third, and fourth windings 1005, 1007, 1011, 1013 coupled to the spine 1003. As shown in FIG. 10, the first winding 1005 has a first end 1005a coupled to the first attachment member 1001 and a second end (not shown) coupled to the spine 1003. The second winding 1007 has a first end (not shown) attached to the spine 1003 at a same location as the second end of the first winding 1007, but on an opposite side of the spine 1003. The second winding 1007 has a second end 1007b attached to the spine 1003 at a distance apart from the first end. The third winding 1011 has a first end 1011a attached to the spine 1003 at the same location as the second end 1007b of the second winding 1007, but on an opposite side of the spine 1003. The third winding 1011 has a second end 1011b attached to the spine 1003 at a distance apart from the first end 1011a. The fourth winding 1013 has a first end 1013a attached to the spine at the same location as the second end 1011b of the third winding 1011, but on an opposite side of the spine 1003. The fourth winding 1013 has a second end 1013a that is attached to the second attachment member 1009. Thus, in this embodiment, the attachment members 1001, 1009 are not directly coupled to the spine 1003.

The attachment members 1001, 1009, which can be shaped as loops, can each mate with a respective deployable implant (e.g., by receiving the implant therein) such that, when the implant is deployed, the device 1000 is anchored to tissue at the vicinity of the body orifice, such as a pyloric opening. For example, the first attachment member 1001 can mate to a first implant (e.g., the first implant 802 in FIG. 8, not shown in FIG. 10) and the second attachment member 1009 can mate to a second implant. The device 1000 can be implanted such that the connector 1004 can at least partially extend across the pyloric opening and can be used to adjust a distance between the attachment members 1001, 1009 after the device 1000 is affixed to tissue in the vicinity of the pyloric opening.

After the device 1000 has been implanted to restrict a size of the pyloric opening (or other body orifice), if a subsequent increase in the size of the opening is desired, one of a first portion 1018 or a second portion 1020 of the spine 1003 can be cut or otherwise broken (and/or removed) such that the distance between the attachment members 1001, 1009 mated to the deployed implants increases. In the illustrated embodiment, if the first portion 1018 of the spine 1003 is cut, the first and second ends (only second end 1007b is shown) of the second winding 1007 will be allowed to move apart, thereby increasing a distance between the first and second attachment members 1001, 1009. If the second portion 1020 of the spine 1003 is cut, the first and second ends 1011a, 1011b of the third winding 1011 will be allowed to move apart, thereby increasing a distance between the first and second attachment members 1001, 1009. If both portions 1018, 1020 are cut, the attachment members 1001, 1009 will move further apart.

If no restriction on the size of the body orifice is required, the first winding 1001 or the fourth winding 1013 can be cut to entirely separate the attachment members 1001, 1009 from one another. It should be appreciated that the spine 1003 can be cut at any point between the ends of the windings to adjust the distance between the attachment members 1001, 1009. For example, in some cases, the second winding 1007 and the portion 1018 of the spine 1003 can both be cut to entirely separate the attachment members 1001 and 1009 from one another. In other cases, the winding 1011 and the portion 1020 of the spine 1003 can both be cut to entirely separate the attachment members 1001 and 1009 from one another. Furthermore, it should be appreciated that the points at which the device 1000 can be cut are shown by way of example only.

One skilled in the art will appreciate that the device 1000 can include any number of windings (e.g., three, five, or more than five) so that the device 1000 can be cut once, twice, or more than twice to thus adjust a size of a body orifice in multiple steps. In addition, the device 1000 can include any other features, such as any of the features of the devices 700, 800, as well as other suitable features.

Figure 11A:
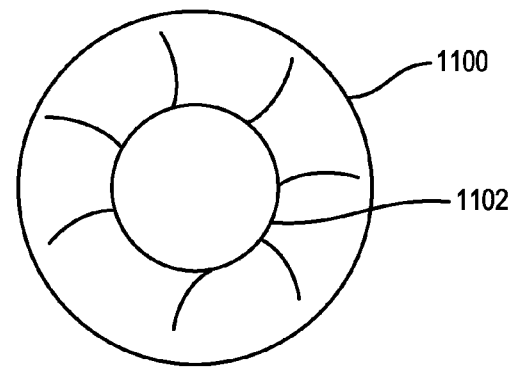
FIG. 11A is a schematic illustration of a pylorus.
Figure 11B:
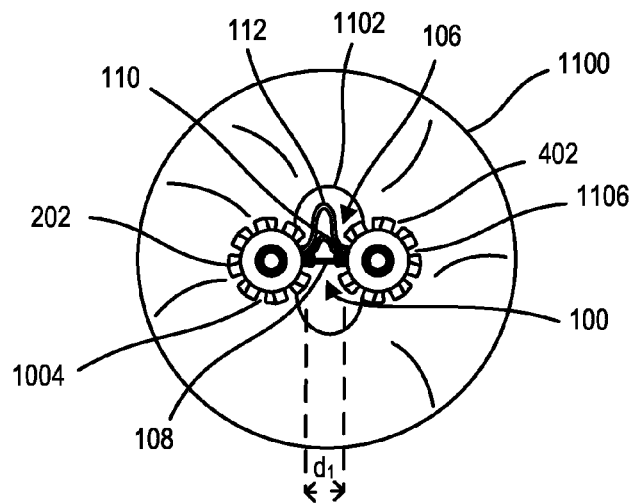
FIG. 11B is a schematic illustration of one embodiment of a method of controlling a size of the pylorus of FIG. 11A.
Figure 11C:
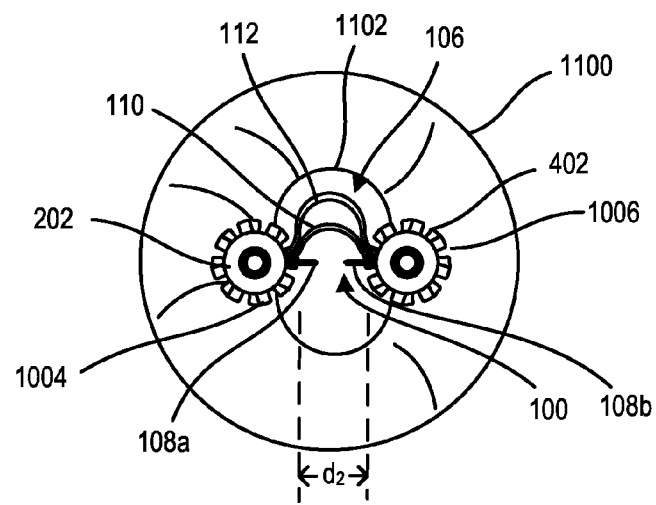
FIG. 11C is another schematic illustration of the method of controlling the size of the pylorus of FIG. 11A.

FIGS. 11A-11C illustrate schematically one embodiment of a method of using a device described herein, such as the device 100 shown in FIGS. 1A-1C and 2-6. FIG. 11A is a schematic illustration of a pylorus 1100 having a pyloric orifice or opening 1102 unrestricted so that the pyloric opening 1102 has its natural size. The pyloric opening is a sphincter, or valve, formed as a ring of smooth muscle, and it should be appreciated that the pyloric opening 1102 is shown in FIGS. 11A-11C very schematically.

FIG. 11B illustrates that the device 100 can be implanted in the vicinity of the pyloric opening 1102 and can be used to control the size thereof. As shown in FIG. 11B, first and second deployable implants, such as the first and second implants 202, 402, can be deployed into tissue at respective opposite first and second sides 1104, 1106 of the pyloric opening 1102. As discussed above, the device 100 can be first anchored into tissue (e.g., at the first side 1104 of the pyloric opening 1102) by deploying a first deployable implant mated to an attachment member of the device, such as the first deployable implant 202 mated to the attachment member 102.

After the device 100 is anchored into tissue at the first side 1104, the device 100 can be tensioned and placed such that the connector 106 extends across the pyloric opening 1102, as shown in FIG. 11B. The second implant 402 can then be deployed and affixed at the opposite second side 1106 of the pyloric opening 1102. In this way, the device 100 is positioned to adjust the size of the pyloric opening 1102. It should be appreciated that the device 100 can be first anchored into tissue at the second side 1106 and then affixed to tissue at the first side 1104. It should also be appreciated that the implants 202, 402 can be affixed into any location in the vicinity of the pyloric opening 1102, as the described techniques are not limited to any specific location at which the implants 202, 402 (or any other implants utilized additionally or alternatively) can be affixed into tissue.

The rear views of the first and second implants 202, 402 are shown in FIGS. 11B and 11C, which are similar to the views of the implants 202, 402 shown in FIG. 6. Thus, the attachment members 102, 104 of the device 100 mated to the first and second implants 202, 402, respectively, are not shown in FIGS. 11B and 11C, and the first and second implants 202, 402 are shown in a deployed configuration.

As schematically shown in FIG. 1B, a distance between the attachment members 102, 104 can be controlled by cutting the portions 108, 110, 112 of the connector 106 which have different lengths. Thus, as shown in FIG. 1A (which does not illustrate deployable implants), the initial distance between the attachment members 102, 104 after the implants 202, 402 have been deployed can be a first distance $d_1$ as set by the length of the first portion 108 of the connector 106 which is the shortest portion thereof.

FIG. 11B shows that the size of the pyloric opening 1102 can be initially restricted by setting the first distance $d_1$ between the implants 202, 402 which can be the same or substantially the same as the distance between the attachment members 102, 104. As also shown in FIG. 1A, the first distance $d_1$ is set by the length of the first portion 108 of the connector 106. Thus, the length of the shortest portion of the connector 106 of the device 100 can be used to define the initially desired distance between the first and second attachment members 102, 104, thus determining a degree to which the pyloric opening or other body orifice is narrowed. For example, when the described techniques are used narrow the pyloric opening 1102 as shown in FIGS. 11B and 11C, the length of the first portion 108 can define a size (e.g., a diameter or other dimensions) of the restricted pyloric opening 1102, which is smaller than the natural size of the pyloric opening 1100 shown in FIG. 11. FIG. 11B illustrates that the size of the pyloric opening 1102 is restricted as compared to the natural size of the pyloric opening 1102 shown in FIG. 11A. FIG. 11C illustrates that the size of the pyloric opening 1102 is increased relative to the size of the pyloric opening 1102 shown in FIG. 11B.

In some circumstances, after the size of the body orifice has been restricted, it may be desired to increase the size of the body orifice or revert to its natural size. For example, when the techniques described herein are used to restrict a size of the pyloric opening to facilitate patient's weight loss and thus treat obesity, the initial reduction in the size of the pyloric opening can lead to certain inconvenience to the patient (e.g., vomiting, nausea, and/or other undesirable symptoms). As another example, the initial restriction of the pyloric opening can result in patient's weight loss and it may be no longer necessary to maintain the opening at the initial reduced size. In either of these, or any other circumstances, it may be desirable to increase the size of the restricted orifice.

Regardless of the reason for a subsequent increase in the size of the pyloric opening 1102 restricted using the described techniques, the pyloric opening 1102 can be widened by cutting or otherwise breaking the first portion 108 of the connector 106, as schematically shown in FIG. 11C where the first portion 108 is cut into two portions 108a and 108b. As a result, as shown in FIG. 11C, the distance between the implants 202, 402 can increase to a second distance $d_2$ that depends on the length of the second portion 110 which is the next longest portion of the connector 106, which is also shown in FIG. 1B (no implants are shown). If, for any reason, a further increase in the size of the pyloric opening 1102 is needed, the second portion 110 of the connector 106 can be cut and the distance between the first and second attachment members 102, 104 can further increase, for example, to the distance $d_3$, as shown in FIG. 1C (no implants are shown). If no restriction of the size of the pyloric opening 1102 is desirable, the third portion 112 of the connector 106 can be also cut to thus revert the pyloric opening 1102 to its unrestricted, natural size.

Accordingly, the described embodiments provide simple, adjustable, and reversible techniques for controlling a size of the body orifice. The implants 202, 402 can be configured to close the puncture in the tissue in an efficient manner that allows decreasing damage to the tissue and blood loss. The connector 106 can be made from such a material that ends of cut portions (e.g., ends of the portions 108a and 108b in FIG. 11C resulting from cutting the first portion 108) do not damage surrounding tissue. Accordingly, the size of the body orifice can be controlled in an atraumatic manner. If no constraints on the size of the restricted body orifice are desirable to be imposed and all portions of the connector 106 are cut, the implants 202, 402 can remain in the body and allow for healing of the punctured tissue. As another option, because the proximal and distal wings can be configured to be deployed reversibly and can be collapsed to move to an undeployed configuration, the implants 202, 402 can be removed from the surgical site.

In some embodiments, at least one, some, or all of the portions of the connector 106 and/or the entire device 100 can be bioabsorbable. Additionally or alternatively, one or more components of the implants 202, 402 can be bioabsorbable. Thus, after the connector 106 is no longer used to restrict the size of the orifice, the implants 202, 402 can remain at the surgical site until they are fully or partially absorbed, which can extend for a period of time that is sufficient for the tissue to heal.

Figure 12:
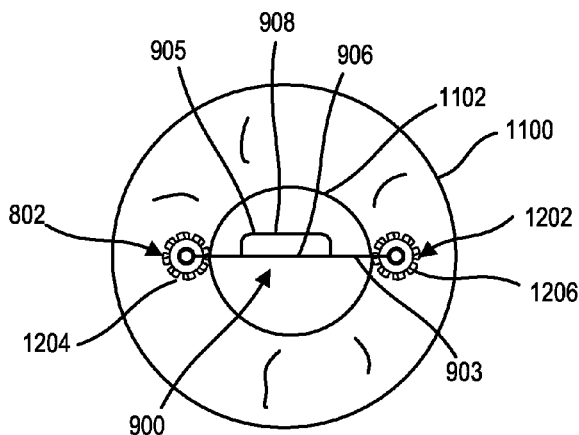
FIG. 12 is a schematic illustration of one embodiment of a method of controlling a size of a pylorus.

FIGS. 12-15 illustrate additional embodiments of a method of using a device for adjusting a size of a pyloric or other orifice. FIG. 12 schematically illustrates the pylorus 1100 with the pyloric opening 1102. In the illustrated embodiment, the device 900 of FIG. 9 is shown by way of a non-limiting example to restrict the size of the pyloric opening 1102.

As shown, the device 900 can be anchored to tissue at the pyloric opening 1102 at a location 1204 using a first deployable implant, such as the implant 802 (FIG. 8). As discussed above, the device 900 can be mated to the implant 802 through a first attachment member (e.g., the attachment member 901 in FIG. 9). After the device 900 is anchored at the location 1204 on one side of the pyloric opening 1102, a second deployable implant 1202 can be received by a second attachment member (e.g., the attachment member 909 in FIG. 9) of the device 900 and tension can be applied to the device 900 to cause the pyloric opening to reduce in size. As shown in FIG. 12, the device 900 can then be affixed to tissue at a location 1206 on the opposite side of the pyloric opening 1102 by deploying the second implant 1202. The implant 1202 can be similar to the implant 802 (e.g., the second implant 402 shown in FIGS. 4-6), or it can be any other suitable implant.

The device 900 can be used to adjust the distance between the first and second implants 802, 1202 if a subsequent increase in the size is required after the size of the pyloric opening 1102 is initially restricted. As discussed above in connection with FIG. 9, the device 900 can be cut along the first bridge portion 905 of the spine 902, and, if no restriction upon the size of the pyloric opening 1102 is required, the device 900 can be further cut along the bracket 906 which forms the second bridge portion.

In some embodiments, more than one device configured to adjust a size of a body orifice in accordance with the described techniques can be utilized. The devices can have any suitable configurations and can be selected such that the size of the orifice can be increased in multiple steps after it has been initially narrowed. For a pylorus, this can allow a more fine-tuned control over a size of food that can be passed from the stomach to the small intestine, which can thus help adjust a rate of gastric emptying with more precision. Furthermore, the patient's anatomy and various conditions may require placing more than one device at the vicinity of the pyloric opening. As another example, when the pyloric opening is narrowed using a first device and it is determined that a further decrease in its size is desired, a second device may be implanted in a suitable manner to further narrow the pyloric opening.

Accordingly, FIG. 13 illustrates one embodiment of a method of using more than one device for adjusting a size of the pyloric opening 1102. As discussed above, a single implant can be used to anchor more than one device as described herein to tissue. Thus, in the embodiment of FIG. 13, a single first implant 1301 can be used to simultaneously anchor both devices 900, 1300 to tissue at a location 1304 on one side of the pyloric opening 1102. In this exemplary embodiment, the device 1300 is shown as having the same configuration as the device 900. However, the device 1300 can have any suitable configuration which can be different than a configuration of the device 900. The devices 900, 1300 can be delivered to the implantation site 1304 in any suitable manner, for example, by being mated to the first implant 1301 via their respective attachment members. In embodiments where at least one of the devices 900, 1300 is configured to conform to a shape and/or size of a delivery assembly coupled to a proximal end of the first implant 1301, the device can be mounted on the delivery assembly.

As further shown in FIG. 13, the devices 900, 1300, anchored at the same location 1304 on one side of the pyloric opening 1102 using the first implant 1301, can be affixed to tissue at respective different locations or sites 1306, 1308 on the opposite side of the pyloric opening 1102 using respective second implants 1202, 1302. The devices 900, 1300 can be positioned in any suitable manner so as to narrow the pyloric opening 1102, and, if desired, can each be cut at one or more portion thereof to subsequently increase the size of the initially narrowed pyloric opening 1102.

Figure 14:
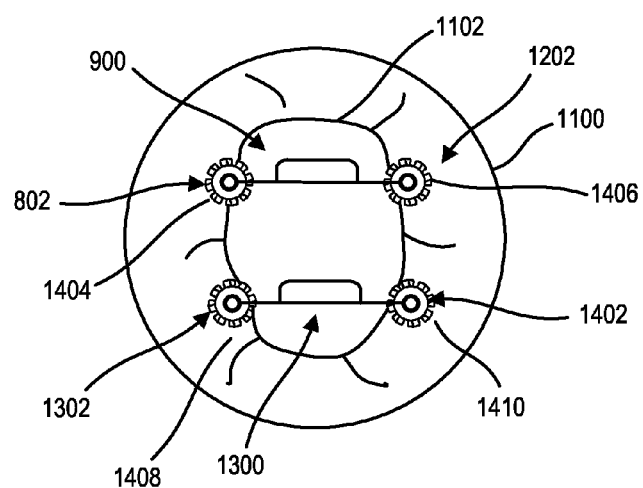
FIG. 14 is a schematic illustration of another embodiment of a method of controlling a size of a pylorus.

FIG. 14 schematically illustrates one embodiment of a method of adjusting a size of the pyloric opening 1102 using more than one device in accordance with the described techniques. In the illustrated embodiment, the devices 900, 1300, each affixed to tissue around the pyloric opening 1102 using respective first and second implants 802, 1202 (the device 900) and 1302, 1402 (the device 1300), can be used to narrow the pyloric opening 1102. As shown in FIG. 14, the first implants 802, 1302 can be used to anchor the devices 900, 1300 at respective locations 1404, 1408 on one side of the pyloric opening 1102, and the second implants 1202, 1402 can be used to anchor the devices 900, 1300 at respective locations 1406, 1410 on the opposite side of the pyloric opening 1102.

Figure 15:
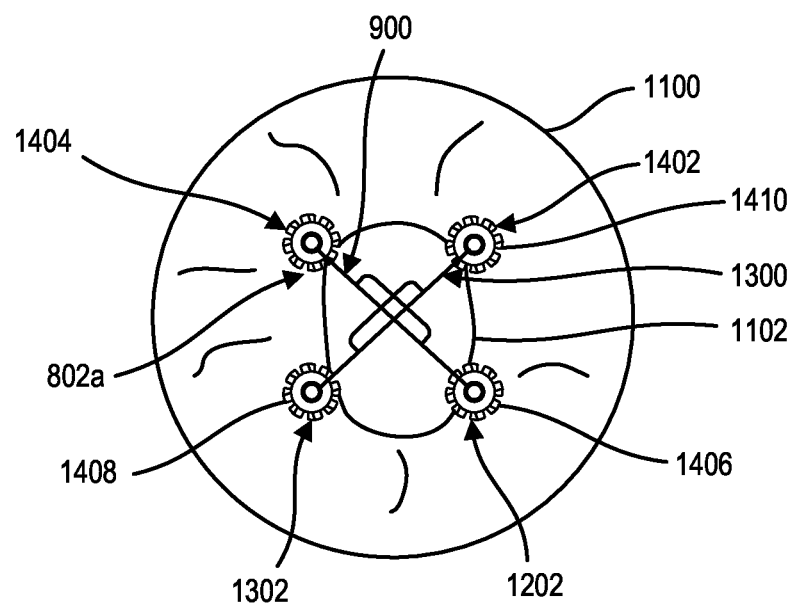
FIG. 15 is a schematic illustration of another embodiment of a method of controlling a size of a pylorus.

One skilled in the art will appreciate that the devices 900, 1300 can be any types of devices, including devices having different configurations. Furthermore, one skilled in the art will appreciate that the devices 900, 1300 can be placed so as to extend across the pyloric opening along a diameter thereof or in any other location of the pyloric opening 1102 (e.g., along any chord thereof), to adjust its size as discussed herein. FIG. 15 schematically illustrates another embodiment of a method of adjusting a size of the pyloric opening 1102 using multiple devices. In this embodiment, as shown in FIG. 15, the devices 900, 1300 can be placed such that they extend across the pyloric opening 1102 in a criss-cross manner. As in FIG. 15, device 900 is affixed to tissue using the first and second implants 802, 1202 at the respective locations 1404, 1406, and device 1300 is affixed to tissue using the first and second implants 1302, 1402 at the respective locations 1408, 1410.

The devices 900, 1300 can be implanted in any order and device 1300 can be placed over device 900, or vice versa. Furthermore, the devices 900, 1300 can be implanted such that they cross each other at any point, as the criss-cross manner of implanting these devices is shown in FIG. 15 by way of a non-limiting example only.

It should be appreciated that any number of devices (e.g., two, three or more) can be implanted in any manner to tissue in the vicinity of a pyloric opening and used to adjust a size thereof. The devices can be implanted to adjustably maintain any suitable distance between opposite sides of the pyloric opening. One or more devices can be implanted so as to form different patterns of the connectors of the devices extending across the pyloric opening. It should also be appreciated that the devices 900, 1300 are shown in FIGS. 12-15 as having a similar configuration by way of example only, as devices having other configurations, including different configurations, can be used additionally or alternatively. As another variation, the devices can be delivered to the implantation site and affixed to tissue in any manner, using any suitable deployable implants.

Figure 16A:
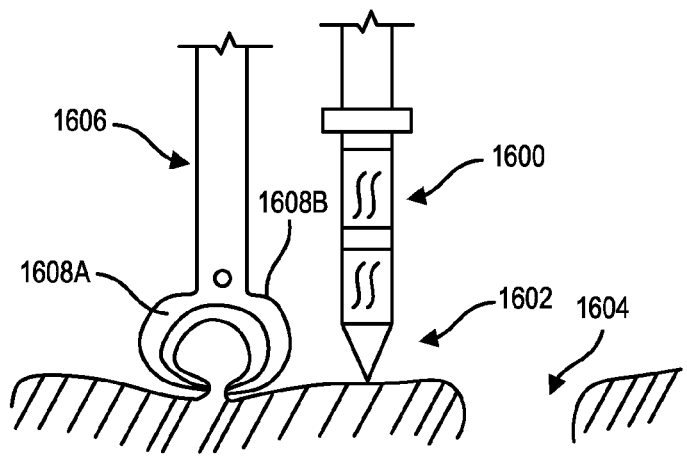
FIG. 16A is a schematic illustration of one embodiment of a method of delivering an implant to an implantation site.
Figure 16B:
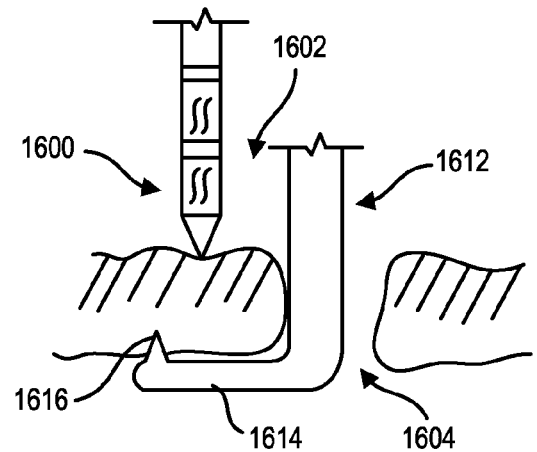
FIG. 16B is another schematic illustration of one embodiment of a method of delivering an implant to an implantation site.
Figure 16C:
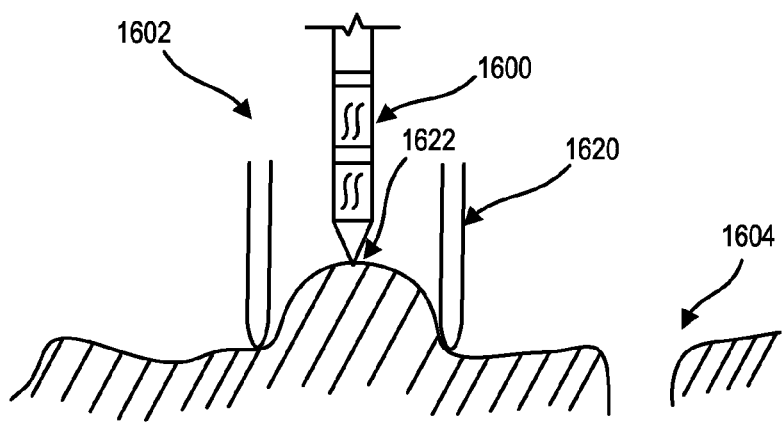
FIG. 16C is another schematic illustration of one embodiment of a method of delivering an implant to an implantation site.

FIGS. 16A-16C illustrate embodiments of a method of delivering an implant 1600 to an implantation site 1602, and in particular, methods of stabilizing or immobilizing tissue at the implantation site 1602 for delivery of the implant 1600. The implant 1600 can be associated with any of the devices as described herein (e.g., devices 100, 700, 900, 1000) which are not shown in FIGS. 16A-16C. In the illustrated embodiments, the implant 1600 can be used to control a size of a pyloric opening 1604. However, one skilled in the art will appreciate that a size of any other opening can be controlled in the described manner. The implant 1600 can be similar to any of implants 202, 402, and 802 (FIGS. 2-6 and 8), or it can be any other device configured to be affixed into tissue.

As shown in FIGS. 16A-16C, the method of delivering the implant 1600 in an undeployed configuration (e.g., prior to deploying proximal and distal wings thereof) to the implantation site 1602 can include grasping and stabilizing a portion of tissue adjacent to a site to be pierced by a distal end of the implant 1600. As shown in FIG. 16A, a portion of the tissue adjacent to the pyloric opening 1604 and located farther from the pyloric opening 1604 than the site to be pierced can be grasped using a suitable grasping instrument 1606. It should be appreciated that tissue at other location(s) adjacent to the site to be pierced by the implant 1600 can be grasped. In the illustrated embodiment, the grasping instrument 1606 (e.g., a pincer, forceps, or other device) includes distal jaws 1608A, 1608B that can be inwardly curved for grabbing tissue therebetween. However, the grasping instrument 1606 can be any suitable instrument configured to grasp tissue and can operate in any suitable manner.

Regardless of the specific configuration of the grasping instrument used, when a portion of the tissue is grasped using such instrument, the tissue at the site to be pierced by the implant 1600 can be tensioned and stabilized to facilitate implant delivery. Further, while the grasped tissue is being held in position using the grasping instrument 1606, the implant 1600 in the undeployed configuration can be delivered to tissue using a suitable delivery device (not shown) so that a distal (forward) end of the implant 1600 penetrates tissue. The grasping instrument 1606 can then be removed. Alternatively, it can remain at the implantation site until distal and proximal wings of the implant 1600 are deployed and the implant 1600 is ejected from a delivery device. In other embodiments, the grasping instrument 1606 can be removed from the surgical site at any time during deployment of the implant 1600.

FIG. 16B illustrates an embodiment in which a retention device 1612 can be used to hold tissue in position. As shown, the retention device 1612 can be advanced (e.g., distally) through the pyloric opening 1604 so that a distal curved portion 1614 of the retention device 1612 is positioned on an opposite side of a tissue wall to be pierced by the implant 1600. After positioning the device 1612 in this manner, it can then be pulled back (e.g., proximally) against the pyloric canal or sphincter to thus help to immobilize the tissue at the implantation site 1612. The retention device 1612 can be any suitable device. Thus, although a T-shaped device is illustrated, the retention device 1612 can have other configurations. As shown in FIG. 16B, the retention device 1612 can have one or more surface features, such as a barb 1616 or other penetrating feature (e.g., tooth, prong, spike, etc.), that can help to stabilize tissue and to prevent its movement during penetration by the implant 1600. The retention device 1612 can remain at the implantation site for any suitable time period. For example, the retention device 1612 can be removed after distal and proximal wings of the implant 1600 are deployed and the implant 1600 is ejected from a delivery device.

As another exemplary embodiment, FIG. 16C illustrates schematically that a suitable suction device 1620 can be used to grasp tissue around a site 1622 to be punctured by the implant 1600. The suction device 1620 can be any suitable device configured to create and maintain suction. While suction is maintained using the suction device 1620, the implant 1600 in the undeployed configuration can be pushed toward the tissue to penetrate it with the distal end of the implant 1600. The suction device 1620 can be removed after distal and proximal wings of the implant 1600 are deployed and prior to or after the implant 1600 is ejected from a delivery device. One skilled in the art will appreciate that devices 1606, 1612, 1620 in FIGS. 16A-16C are shown by way of example only and that any type of device(s) can be used to immobilize tissue at the implantation site to facilitate delivery of an implant into tissue.

Regardless of the configuration of a utilized device, the described procedures resulting in narrowing of the pylorus can delay gastric emptying and therefore lead to early feeling of satiation. The described techniques for controlling a size of a body orifice, such as a pylorus, can be used for treating a subject in need thereof. As used herein, a subject can be a mammal, for example, human, a non-human primate, a horse, a sheep, a cat, a dog, a cow, a pig, or other mammal. For example, a subject can be a human patient or an animal that has been diagnosed with obesity or other disorder associated with excessive weight. A subject can experience reduction in appetite and feel satiation after food consumption sooner than this would normally happen. In this way, an eating behavior of the subject can be changed, which can lead to a decrease in food consumption and, ultimately, to weight loss.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for controlling a size of an orifice, comprising:
   a first implant configured to be implanted within tissue;
   a second implant configured to be implanted within tissue;
   a connector having a first end coupled to the first implant and a second end coupled to the second implant, the connector including
   a first bridge portion extending between the first and second ends and having a first length, the first bridge portion being configured to maintain the first and second implants at a first distance apart from one another, and
   a second bridge portion extending between the first and second ends and having a second length that is greater than the first length, the second bridge portion being configured to maintain the first and second implants at a second distance apart from one another;
   wherein the first bridge portion is configured to control the size of the orifice by having the first bridge portion be cut at a location along the first length so as to form free ends at opposed sides of the location, and wherein the cutting of the first bridge portion allows the first and second implants to move from the first distance apart to the second distance apart.

2. The system of claim 1, wherein the connector includes at least one loop formed thereon that is configured to slidably receive one of the first and second implants.

3. The system of claim 1, wherein the connector includes a first loop formed on the first end thereof and configured to slidably receive the first implant, and the connector includes a second loop formed on the second end thereof and configured to slidably receive the second implant.

4. The system of claim 1, further comprising a third bridge portion extending between the first and second ends of the connector and having a third length that is greater than the second length, the third bridge portion being configured to maintain the first and second implants at a third distance apart, and wherein, with the first bridge portion cut, the second bridge portion is configured to be cut to allow the first and second implants to move from the second distance apart to the third distance apart.

5. The system of claim 1, wherein the first bridge portion is positioned between opposed ends of the second bridge portion.

6. The system of claim 1, wherein at least one of the first and second implants comprises proximal and distal deployable wings configured to engage tissue therebetween.

7. The system of claim 1, wherein the connector includes a first attachment member formed on the first end thereof for coupling with the first implant, and the connector includes a second attachment member formed on the second end thereof for coupling with the second implant.

8. The system of claim 7, wherein at least one of the first and second attachment members is configured to slidably receive at least one of the first and second implants.

9. The system of claim 7, wherein the connector includes a third attachment member configured to couple with a third implant, the third implant configured to be implanted within tissue.

10. The system of claim 9, wherein at least one of the second and third implants is configured to receive a delivery tool therethrough, the delivery tool being used to deliver the at least one of the second and third implants to the orifice.

11. The system of claim 1, wherein the connector comprises a spine extending between the first and second implants.

12. The system of claim 11, wherein the spine is directly coupled to the first and second implants.

13. The system of claim 11, wherein the second bridge portion comprises a bracket having first and second ends thereof coupled to the spine.

14. The system of claim 13, wherein the first bridge portion is defined by a portion of the spine extending between the first and second ends of the bracket, and wherein the second bridge portion is defined by the bracket.

15. The system of claim 11, wherein the spine defines the first bridge portion, and wherein a first end of the second bridge portion and a second end of the second bridge portion are coupled to the spine.

16. The system of claim 11, wherein the connector includes a plurality of windings coupled to the spine.

* * * * *